US012478517B2

(12) United States Patent
Bishop et al.

(10) Patent No.: US 12,478,517 B2
(45) **Date of Patent: *Nov. 25, 2025**

(54) ABSORBENT ARTICLE WITH SELECTIVELY POSITIONED WAIST CONTAINMENT MEMBER

(71) Applicant: Kimberly-Clark Worldwide, Inc., Neenah, WI (US)

(72) Inventors: David F. Bishop, Appleton, WI (US); Patsy A. Benedict, Omro, WI (US); Joseph D. Coenen, Kaukauna, WI (US); Kaitlyn E. Mast, Shipshewana, IN (US); Michael J. Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,533

(22) Filed: Feb. 22, 2023

(65) Prior Publication Data

US 2023/0190542 A1 Jun. 22, 2023

Related U.S. Application Data

(63) Continuation of application No. 15/556,721, filed as application No. PCT/US2015/023620 on Mar. 31, 2015, now Pat. No. 11,612,522.

(51) Int. Cl.

| | |
|---|---|
| ***A61F 13/494*** | (2006.01) |
| ***A61F 13/495*** | (2006.01) |
| ***A61F 13/496*** | (2006.01) |

(52) U.S. Cl.

CPC ...... *A61F 13/49466* (2013.01); *A61F 13/495* (2013.01); *A61F 13/496* (2013.01);

(Continued)

(58) Field of Classification Search

CPC .... A61F 13/49; A61F 13/49011; A61F 13/84; A61F 13/58; A61F 13/49466;

(Continued)

(56) References Cited

U.S. PATENT DOCUMENTS 3,395,708 A 8/1968 Laurence et al.
3,800,796 A 4/1974 Jacob (Continued)

FOREIGN PATENT DOCUMENTS

CN 1200662 A 12/1998
CN 1853592 A 11/2006

(Continued)

*Primary Examiner* — Nicholas J. Weiss
*Assistant Examiner* — Gabriella E Burnette
(74) *Attorney, Agent, or Firm* — KIMBERLY-CLARK WORLDWIDE, INC.

(57) ABSTRACT

An absorbent article (10, 110, 210, 310) can include a chassis (11) including an absorbent body (34). The chassis (11) can include a body facing surface (19). The absorbent article (10, 110, 210, 310) can also include a waist containment member (54, 154, 254). The waist containment member (54, 154, 254) can include a proximal portion (76) coupled to the body facing surface (19) of the chassis (11) and a distal portion (78) that includes a free edge (88). The distal portion (78) can be free to move with respect to the chassis (11) when the absorbent article (10, 110, 210, 310) is in a relaxed configuration. The free edge (88) can be about 50.0 millimeters or less from the rear waist edge (24) of the absorbent article (10, 110, 210, 310) when the absorbent article (10, 110, 210, 310) is in the stretched, laid-flat configuration.

20 Claims, 19 Drawing Sheets

(52) U.S. Cl.
CPC ................. *A61F 2013/4948* (2013.01); *A61F 2013/49493* (2013.01)

(58) Field of Classification Search
CPC ............ A61F 13/54798; A61F 13/5622; A61F 13/627; A61F 2013/49098; A61F 2013/49493; A61F 2013/55125; A61F 2013/5683; A61F 2013/8402
See application file for complete search history.

(56) References Cited

U.S. PATENT DOCUMENTS 3,848,594 A 11/1974 Buell
3,860,003 A 1/1975 Buell
3,930,501 A 1/1976 Schaar
3,978,861 A 9/1976 Schaar
3,995,640 A 12/1976 Schaar
4,074,716 A 2/1978 Schaar
4,525,407 A 6/1985 Ness
4,642,110 A 2/1987 Dudek
4,643,729 A 2/1987 Laplanche
4,657,539 A 4/1987 Hasse
4,657,802 A 4/1987 Morman
4,681,579 A 7/1987 Toussant et al.
4,735,624 A 4/1988 Mazars
4,738,677 A 4/1988 Foreman
4,741,949 A 5/1988 Morman et al.
4,753,646 A 6/1988 Enloe
4,808,176 A 2/1989 Kielpikowski
4,808,177 A 2/1989 DesMarais et al.
4,822,435 A 4/1989 Igaue et al.
4,850,990 A 7/1989 Huntoon et al.
4,935,021 A 6/1990 Huffman et al.
4,938,755 A 7/1990 Foreman
4,977,011 A 12/1990 Smith
5,026,364 A 6/1991 Robertson
5,064,421 A 11/1991 Tracy
5,069,672 A 12/1991 Wippler et al.
5,106,385 A 4/1992 Allen et al.
5,151,091 A 9/1992 Glaug et al.
5,151,092 A * 9/1992 Buell .................. A61F 13/4902 604/385.3
5,187,817 A 2/1993 Zolner
5,209,801 A 5/1993 Smith
5,366,452 A 11/1994 Widlund et al.
5,397,318 A 3/1995 Dreier
5,413,570 A 5/1995 Enloe
5,439,459 A 8/1995 Tanji et al.
5,451,219 A 9/1995 Suzuki et al.
5,514,104 A 5/1996 Cole et al.
5,514,121 A 5/1996 Roe et al.
5,531,730 A 7/1996 Dreier
5,540,671 A 7/1996 Dreier
5,558,660 A * 9/1996 Dreier ............... A61F 13/49413 604/385.19
5,558,661 A 9/1996 Roe et al.
5,569,227 A 10/1996 Vandemoortele et al.
5,582,606 A 12/1996 Bruemmer et al.
5,593,401 A * 1/1997 Sosalla ............... A61F 13/5644 604/385.28
5,624,422 A 4/1997 Allen
5,643,242 A 7/1997 Lavon et al.
5,649,918 A 7/1997 Schleinz
5,667,503 A 9/1997 Roe et al.
5,672,166 A 9/1997 Vandemoortele
5,674,215 A 10/1997 Ronnberg
5,685,873 A 11/1997 Bruemmer
5,690,627 A 11/1997 Clear et al.
5,695,488 A 12/1997 Sosalla
5,776,121 A 7/1998 Roe et al.
5,795,347 A 8/1998 Roe et al.
5,817,086 A 10/1998 Kling
5,827,259 A 10/1998 Laux et al.
5,858,012 A 1/1999 Yamaki et al.
5,895,382 A 4/1999 Popp et al.
5,904,675 A * 5/1999 Laux ................. A61F 13/49009 604/386
5,931,826 A 8/1999 Faulks et al.
5,938,652 A * 8/1999 Sauer .................... A61F 13/495 604/386
5,993,433 A 11/1999 St. Louis et al.
6,103,952 A 8/2000 Coles et al.
6,132,410 A 10/2000 Van Gompel et al.
6,135,988 A 10/2000 Turner et al.
6,142,985 A 11/2000 Feist
6,149,638 A 11/2000 Vogt et al.
6,174,303 B1 1/2001 Suprise et al.
6,217,563 B1 4/2001 Van Gompel et al.
6,258,076 B1 * 7/2001 Glaug ............... A61F 13/49466 604/386
6,264,639 B1 7/2001 Sauer
6,264,641 B1 7/2001 Van Gompel et al.
6,280,426 B1 8/2001 Turner et al.
6,293,937 B2 9/2001 Matsushita et al.
6,306,122 B1 10/2001 Narawa et al.
6,315,764 B1 11/2001 Faulks et al.
6,425,889 B1 * 7/2002 Kitaoka ............ A61F 13/49466 604/385.19
6,443,933 B1 9/2002 Suzuki et al.
6,455,753 B1 9/2002 Glaug et al.
6,458,114 B1 10/2002 Mishima et al.
6,482,194 B1 11/2002 Putzer
6,491,677 B1 12/2002 Glaug et al.
6,494,872 B1 12/2002 Suzuki et al.
6,506,185 B1 1/2003 Sauer et al.
6,527,756 B1 3/2003 Mishima et al.
6,638,262 B2 10/2003 Suzuki et al.
6,648,870 B2 11/2003 Itoh et al.
6,699,228 B1 3/2004 Chmielewski et al.
6,827,806 B2 12/2004 Uitenbroek et al.
6,838,591 B2 1/2005 Waksmundzki et al.
6,881,207 B1 4/2005 Tracy
6,890,327 B2 5/2005 Suzuki et al.
7,066,921 B2 6/2006 Schmoker et al.
7,166,093 B2 1/2007 Drevik et al.
7,166,095 B1 1/2007 Coates
7,247,152 B2 7/2007 Klemp et al.
7,604,625 B2 10/2009 Turi et al.
7,666,173 B2 2/2010 Mishima et al.
7,767,876 B2 8/2010 Davis et al.
7,842,021 B2 11/2010 Wood et al.
7,879,017 B1 2/2011 Tabata et al.
7,993,314 B2 8/2011 Asp et al.
8,075,543 B2 12/2011 Okuda
9,044,359 B2 6/2015 Wciorka et al.
10,010,458 B2 7/2018 Barnes
10,159,610 B2 12/2018 Barnes
11,096,836 B2 8/2021 Bishop et al.
2001/0016720 A1 8/2001 Otsubo
2002/0045878 A1 4/2002 Shimoe et al.
2002/0082570 A1 6/2002 Mishima et al.
2002/0147438 A1 10/2002 Tanaka et al.
2003/0045853 A1 3/2003 Sauer
2003/0050616 A1 3/2003 Reynolds et al.
2003/0109844 A1 6/2003 Gibbs
2003/0119405 A1 6/2003 Abuto et al.
2003/0216705 A1 11/2003 Coates
2004/0002690 A1 1/2004 Miyamoto
2004/0019343 A1 1/2004 Olson et al.
2004/0127882 A1 7/2004 Weber
2004/0243086 A1 12/2004 VanGompel et al.
2005/0027274 A1 2/2005 Suzuki et al.
2005/0148974 A1 7/2005 Datta et al.
2005/0215974 A1 9/2005 Susan
2005/0256488 A1 11/2005 Sperl
2006/0058738 A1 3/2006 Ponzi et al.
2006/0058767 A1 3/2006 Zhang et al.
2007/0093164 A1 4/2007 Nakaoka
2007/0112322 A1 5/2007 Ashton et al.
2007/0255245 A1 11/2007 Asp et al.
2007/0293832 A1 12/2007 Wood et al.
2008/0300560 A1 * 12/2008 Magnusson ....... A61F 13/51305 604/386
2010/0305533 A1 12/2010 Ashton et al.

(56) References Cited

U.S. PATENT DOCUMENTS

| | | | |
|---|---|---|---|
| 2012/0277703 | A1 | 11/2012 | Rhein et al. |
| 2012/0323207 | A1 | 12/2012 | Takaishi |
| 2013/0012905 | A1 | 1/2013 | Katsuragawa et al. |
| 2013/0012906 | A1 | 1/2013 | Takino |
| 2013/0012907 | A1 | 1/2013 | Sasayama et al. |
| 2013/0046266 | A1 | 2/2013 | Kawakami |
| 2014/0018761 | A1 | 1/2014 | Orchard, IV et al. |
| 2014/0121623 | A1 | 5/2014 | Kirby et al. |
| 2014/0128829 | A1 | 5/2014 | Miyake et al. |
| 2014/0257231 | A1 | 9/2014 | Wang et al. |
| 2014/0350504 | A1 | 11/2014 | Popp et al. |
| 2015/0051568 | A1 | 2/2015 | Sakaguchi et al. |
| 2015/0182388 | A1 | 7/2015 | Katsuragawa et al. |
| 2017/0000658 | A1 | 1/2017 | Chatterjee et al. |
| 2017/0128281 | A1 | 5/2017 | Takino et al. |
| 2017/0239104 | A1 | 8/2017 | Jang et al. |
| 2017/0246054 | A1 | 8/2017 | Bishop et al. |
| 2017/0296401 | A1 | 10/2017 | Sugiyama et al. |
| 2018/0055698 | A1 | 3/2018 | Bishop et al. |
| 2018/0071155 | A1 | 3/2018 | Bishop et al. |
| 2018/0104116 | A1 | 4/2018 | Bishop et al. |
| 2019/0083331 | A1 | 3/2019 | Barnes |
| 2020/0038256 | A1 | 2/2020 | Jang et al. |
| 2020/0107973 | A1 | 4/2020 | Bishop et al. |
| 2021/0346212 | A1 | 11/2021 | Bishop et al. |

FOREIGN PATENT DOCUMENTS

| | | | |
|---|---|---|---|
| CN | 102065811 | A | 5/2011 |
| CN | 102065813 | B | 11/2014 |
| CN | 204072501 | U | 1/2015 |
| JP | 2001178772 | A | 7/2001 |
| JP | 4754634 | B2 | 8/2011 |
| KR | 100648562 | B1 | 11/2006 |
| KR | 2020130001181 | U | 2/2013 |
| WO | 9601607 | A1 | 1/1996 |
| WO | 0037008 | A1 | 6/2000 |
| WO | 2013021897 | A1 | 2/2013 |
| WO | 2016159983 | A1 | 10/2016 |

* cited by examiner

ABSORBENT ARTICLE WITH SELECTIVELY POSITIONED WAIST CONTAINMENT MEMBER

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the rear waist region to solve the problems described above. One example is by providing a waist elastic member and not adhering a portion of the waist containment member closest to the lateral axis of the absorbent article to the bodyside liner, such that the non-adhered portion of the waist elastic member can provide a containment pocket for exudates. One example of this configuration is a HUGGIES® Little Snugglers diaper. Although absorbent articles with such containment members intend to prevent leakage of exudates and have functioned adequately, failures can still occur.

Thus, there is a desire for improvements to containment systems and containment members of absorbent articles to prevent leakage of exudates, especially in the waist regions of the absorbent article. There is also a desire for improvements in containment systems to have increased void volumes to hold body exudates until the absorbent article can be changed.

SUMMARY OF THE DISCLOSURE

In one embodiment, an absorbent article can include a front waist region including a front waist edge, a rear waist region including a rear waist edge, a crotch region, a longitudinal axis and a lateral axis. The absorbent article can include a chassis including an absorbent body. The chassis can include a body facing surface. The absorbent article can further include a waist containment member disposed on the body facing surface of the chassis. The waist containment member can include a first longitudinal side edge and a second longitudinal side edge. The waist containment member can further include a proximal portion and a distal portion. The proximal portion can be coupled to the body facing surface of the chassis. The distal portion can include a free edge and can be free to move with respect to the chassis when the absorbent article is in a relaxed configuration. The waist containment member can include at least three folds when the absorbent article is in a stretched, laid-flat configuration. Each of the at least three folds can fold the waist containment member in a direction generally parallel to the lateral axis of the absorbent article.

In another embodiment, an absorbent article can include a front waist region including a front waist edge, a rear waist region including a rear waist edge, a crotch region, a longitudinal axis and a lateral axis. The absorbent article can include a chassis including an absorbent body. The chassis can include a body facing surface. The absorbent article can further include a waist containment member disposed on the body facing surface of the chassis. The waist containment member can include a first longitudinal side edge and a second longitudinal side edge. The waist containment member can also include a proximal portion and a distal portion. The proximal portion can include a first edge and a second edge. The proximal portion can be coupled to the body facing surface of the absorbent assembly. The distal portion can include a free edge and can be free to move with respect to the chassis when the absorbent article is in a relaxed configuration. The second edge of the proximal portion of the waist containment member can define a transition between the proximal portion and the distal portion. The free edge of the distal portion can be closer to the rear waist edge than is the first edge of the proximal portion of the waist containment member when the absorbent article is in a stretched, laid-flat configuration.

In yet another embodiment, an absorbent article can include a front waist region including a front waist edge, a rear waist region including a rear waist edge, a crotch region, a longitudinal axis and a lateral axis. The absorbent article can include a chassis including an absorbent body. The chassis can include a body facing surface. The absorbent article can further include a waist containment member disposed on the body facing surface of the chassis. The waist containment member can include a first longitudinal side edge and a second longitudinal side edge. The waist containment member can further include a proximal portion and a distal portion. The proximal portion can be coupled to the body facing surface of the chassis. The distal portion can include a free edge and can be free to move with respect to the chassis when the absorbent article is in a relaxed configuration. The free edge can be about 50.0 millimeters or less from the rear waist edge of the absorbent article when the absorbent article is in the stretched, laid-flat configuration.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
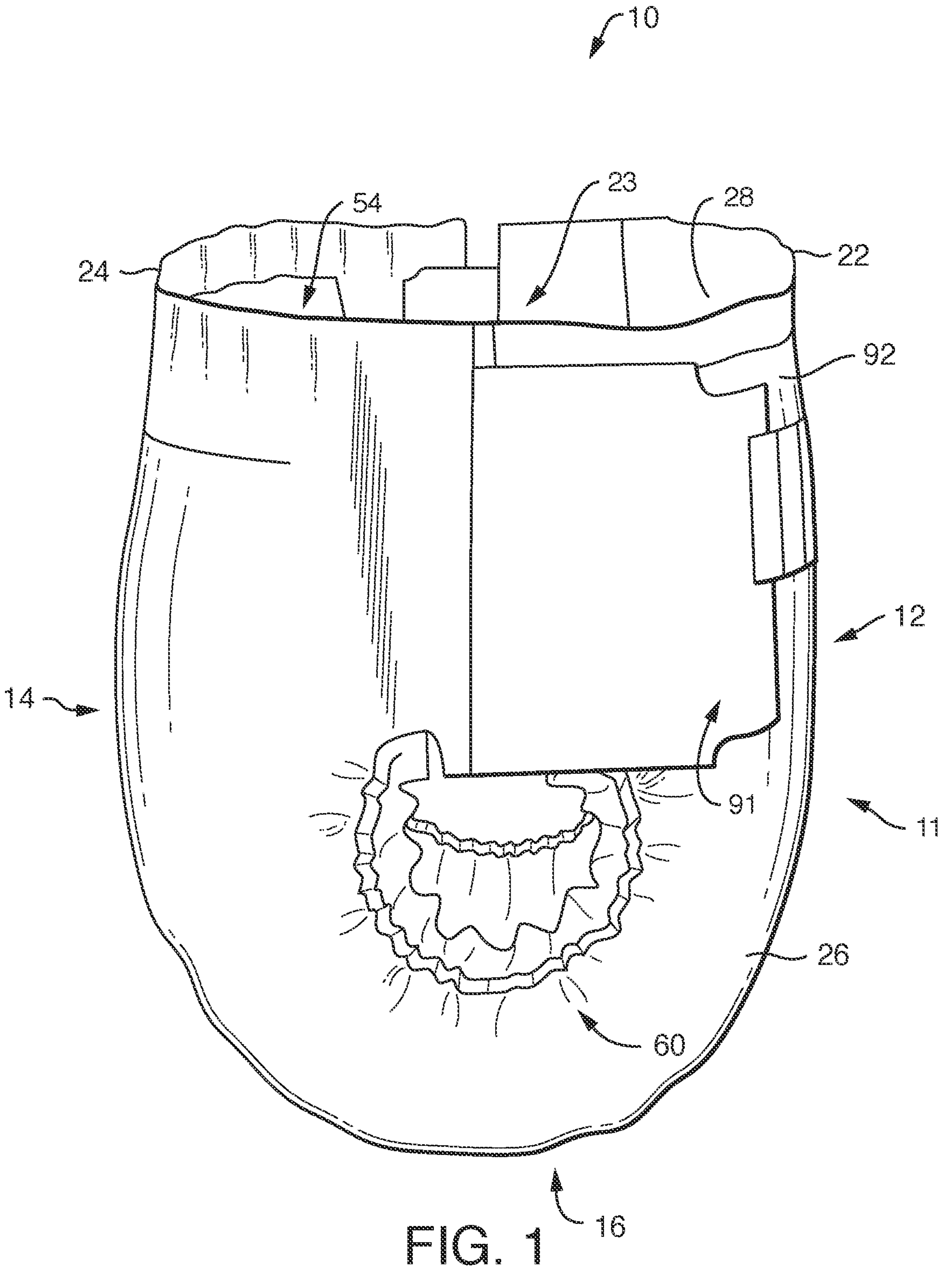
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a waist containment member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-4 and 10-13B, a non-limiting illustration of an absorbent article 10, 110, 210 for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 310 in FIGS. 14 and 15 provides an exemplary embodiment of an absorbent article 310 that can be manufactured in cross-direction manufacturing process.

Figure 2:
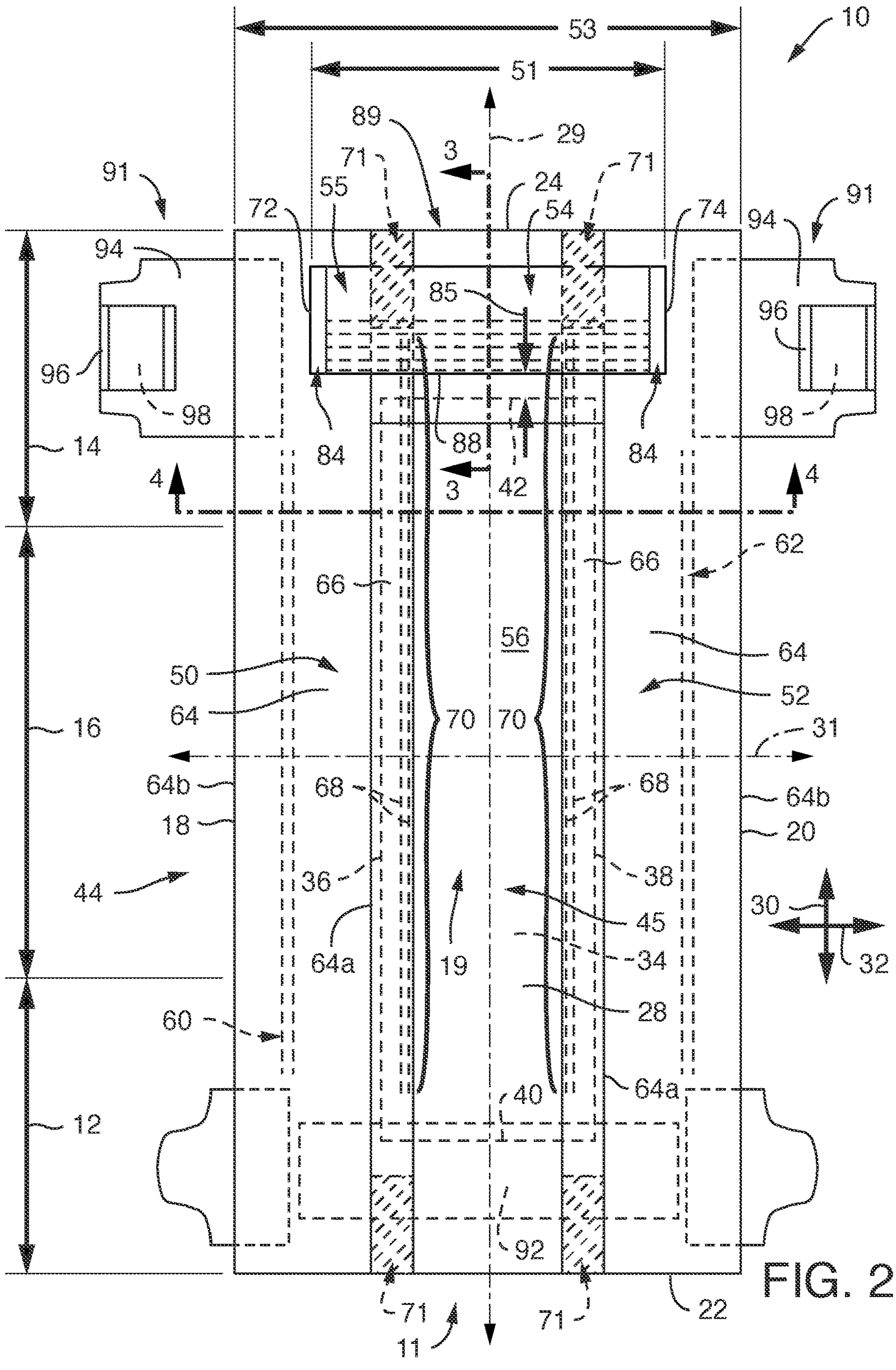
FIG. 2 is a top plan view of the absorbent article of FIG. 1 in a stretched, laid flat, unfastened condition.
Figure 10:
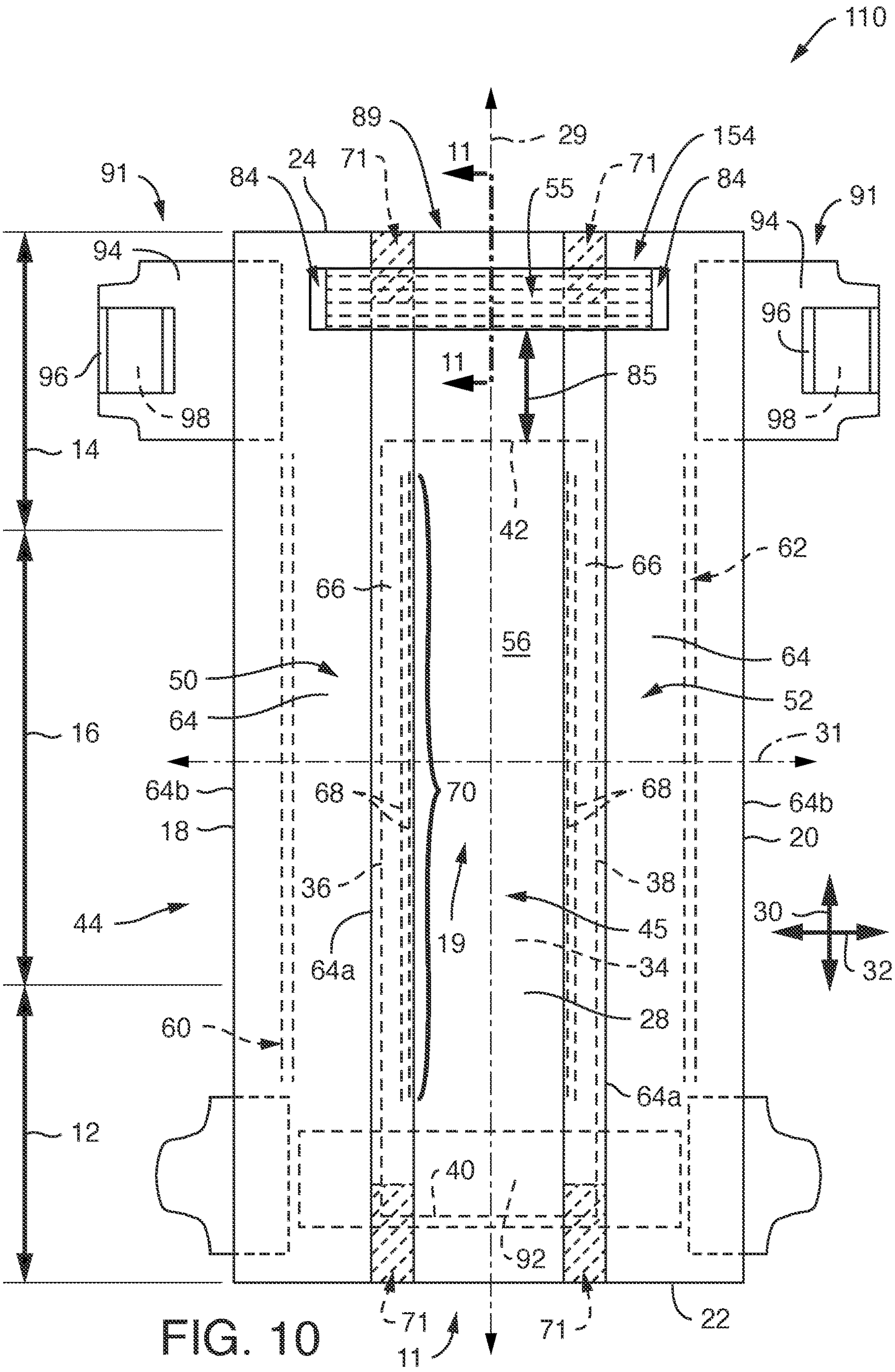
FIG. 10 is a top plan view of an absorbent article with an alternative waist containment member.
Figure 12:
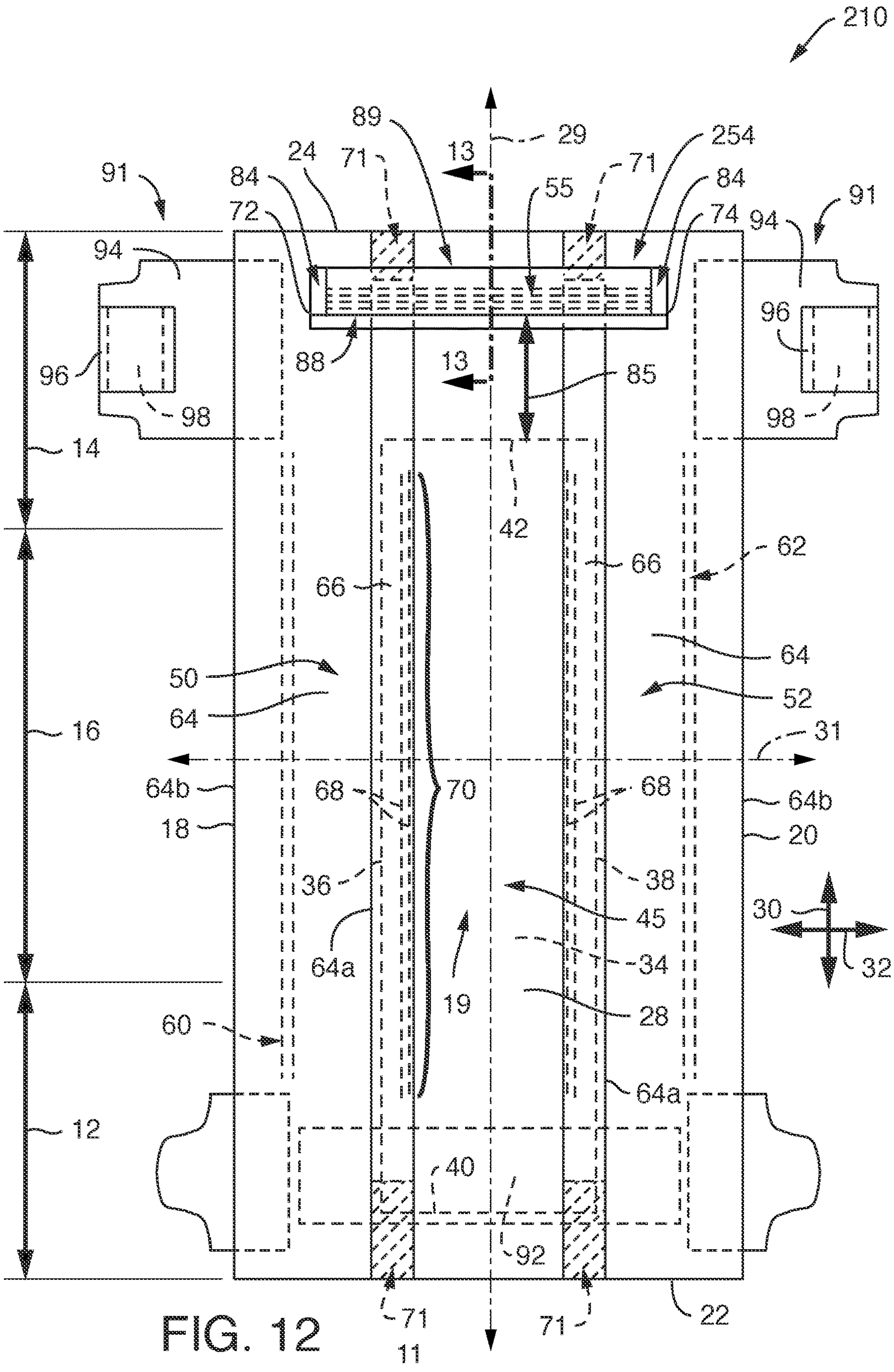
FIG. 12 is a top plan view of an absorbent article with yet another alternative waist containment member.
Figure 14:
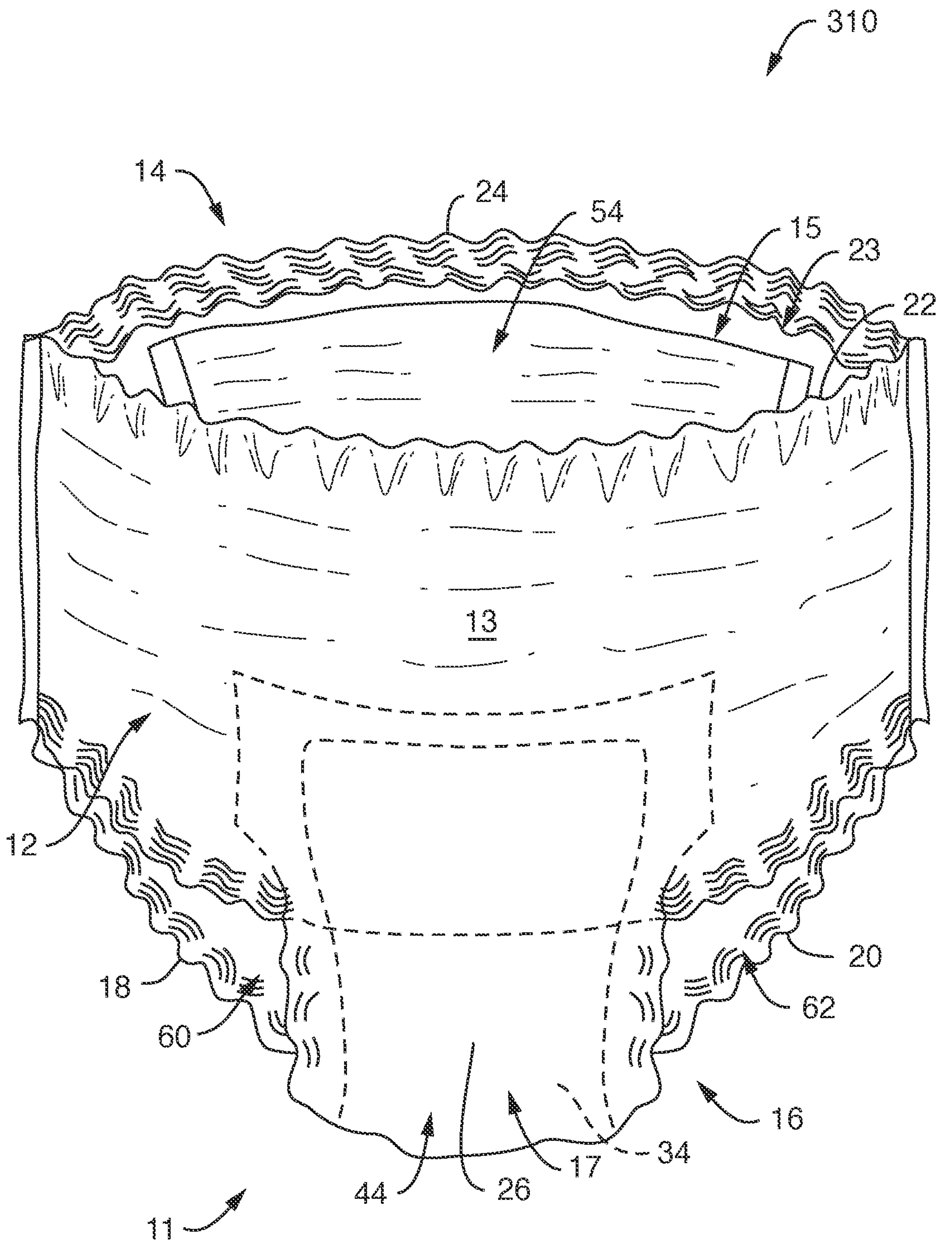
FIG. 14 is a front perspective view of an alternative embodiment of an absorbent article, such as a pant.
Figure 15:
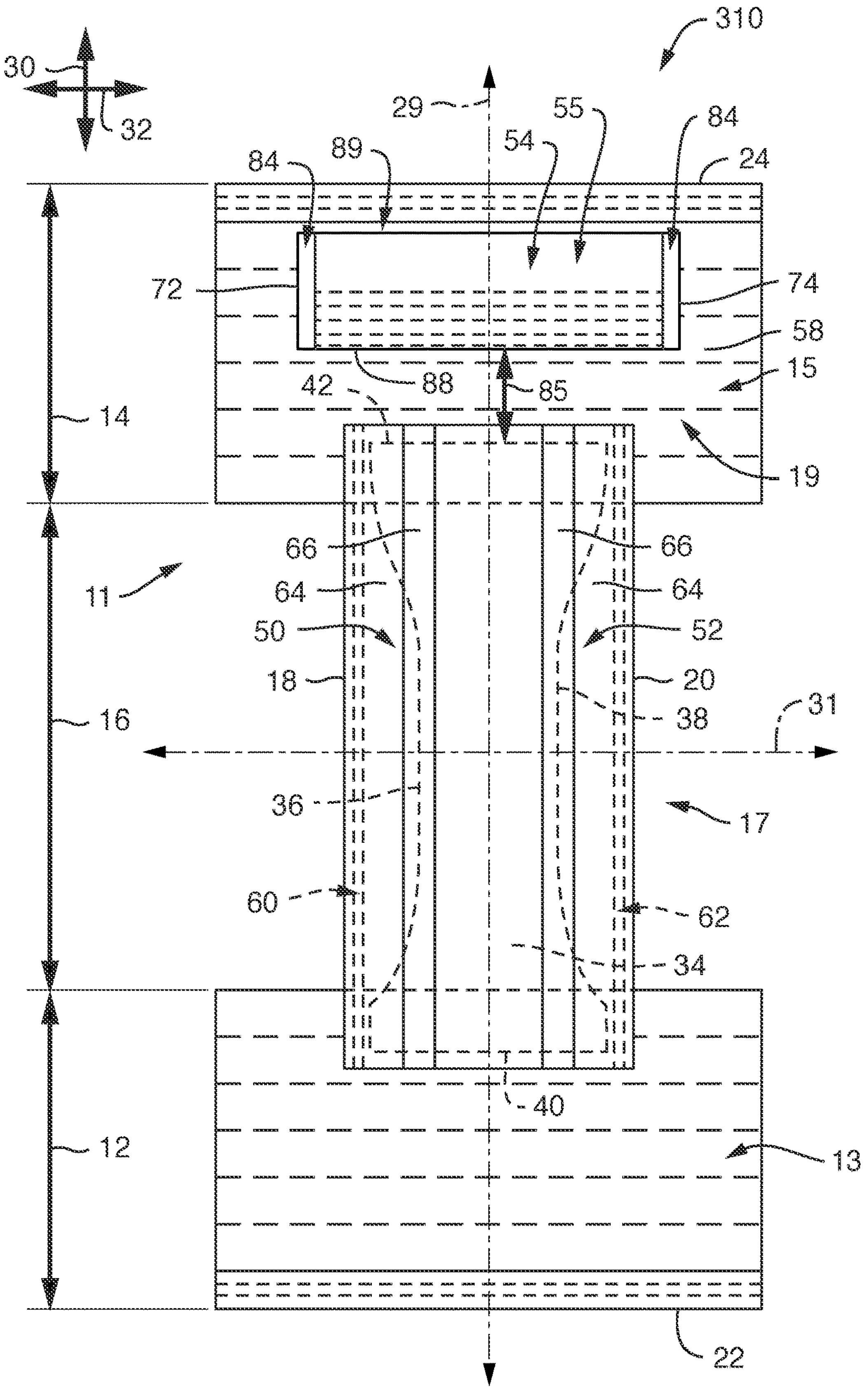
FIG. 15 is a top plan view of the absorbent article of FIG. 14 in a stretched, laid flat condition.

The absorbent article 10 illustrated in FIGS. 1 and 2, the absorbent article 110 illustrated in FIG. 10, the absorbent article 210 illustrated in FIG. 12, and the absorbent article 310 illustrated in FIGS. 14 and 15 can each include a chassis 11. The absorbent article 10, 110, 210, 310 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 14 and 15, a three-piece construction of an absorbent article 310 is depicted where the absorbent article 310 can have a chassis 11 including a front waist panel 13 defining the front waist region 12, a rear waist panel 15 defining the rear waist region 14, and an absorbent panel 17 defining the crotch region 16 of the absorbent article 310. The absorbent panel 17 can extend between the front waist panel 13 and the rear waist panel 15. In some embodiments, the absorbent panel 17 can overlap the front waist panel 13 and the rear waist panel 15.

The absorbent panel 17 can be bonded to the front waist panel 13 and the rear waist panel 15 to define a three-piece construction. However, it is contemplated that an absorbent article can be manufactured in a cross-direction without being a three-piece construction garment.

The absorbent article 10, 110, 210, 310 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 110, 210 illustrated in FIGS. 2, 10, and 12. In other embodiments, the longitudinal side edges 18, 20 can be curved between the front waist edge 22 and the rear waist edge 24. In the absorbent article 310 of FIGS. 14 and 15, the longitudinal side edges 18, 20 can include portions of the front waist panel 13, the absorbent panel 17, and the rear waist panel 15.

The front waist region 12 can include the portion of the absorbent article 10, 110, 210, 310 that, when worn, is positioned at least in part on the front of the wearer while the rear waist region 14 can include the portion of the absorbent article 10, 110, 210, 310 that, when worn, is positioned at least in part on the back of the wearer. The crotch region 16 of the absorbent article 10, 110, 210, 310 can include the portion of the absorbent article 10, 110, 210, 310 that, when worn, is positioned between the legs of the wearer and can partially cover the lower torso of the wearer. The waist edges, 22 and 24, of the absorbent article 10, 110, 210, 310 are configured to encircle the waist of the wearer and together define a central waist opening 23 (as labeled in FIG. 1 and FIG. 14) for the waist of the wearer. Portions of the longitudinal side edges 18, 20 in the crotch region 16 can generally define leg openings for the legs of the wearer when the absorbent article 10, 110, 210, 310 is worn.

Figure 3A:
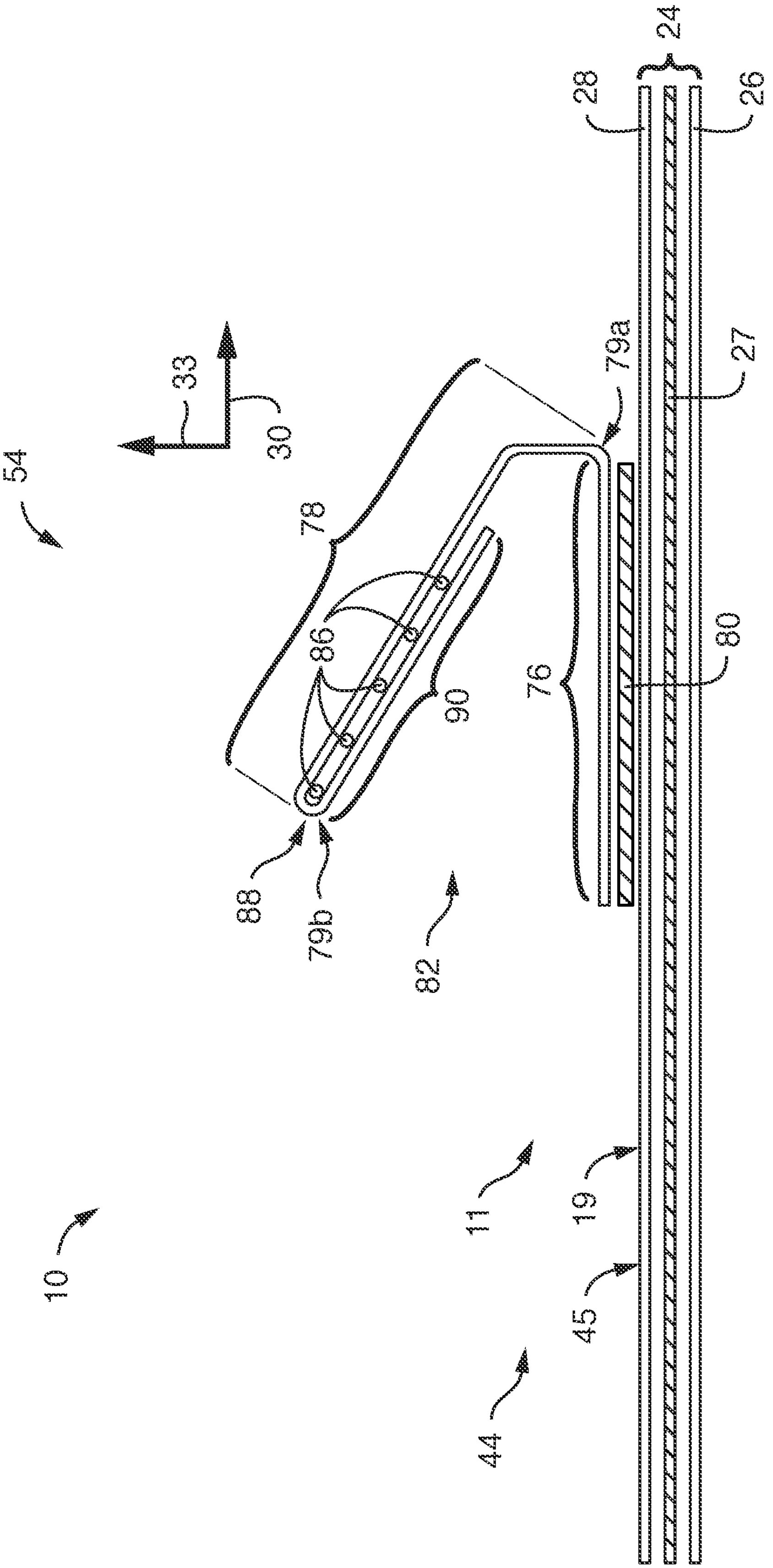
FIG. 3A is a cross-sectional view taken along line 3-3 from FIG. 2, but with the waist containment member being shown in a relaxed configuration.
Figure 3B:
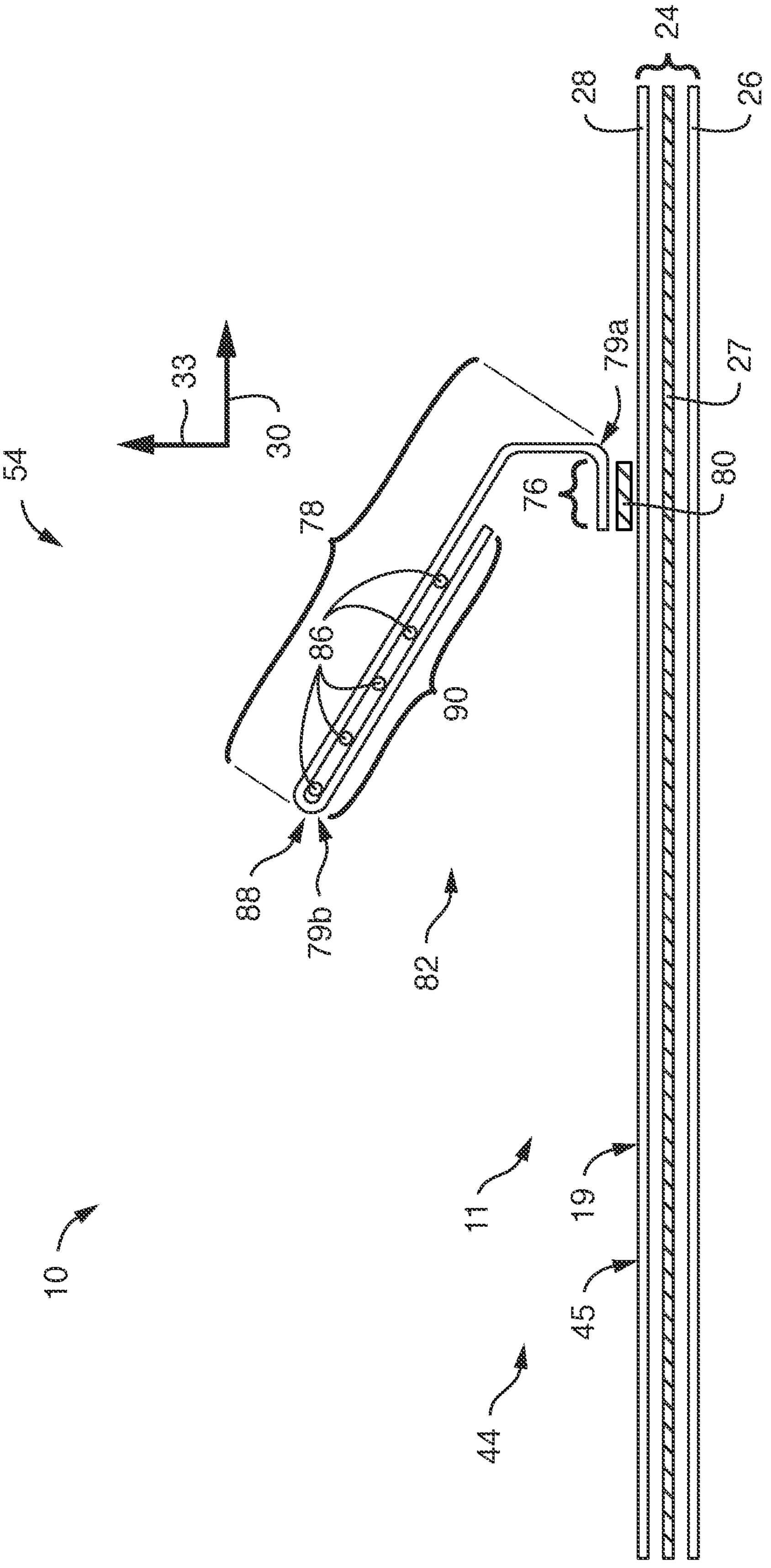
FIG. 3B is a cross-sectional view similar to FIG. 3A, but of an alternative embodiment of a waist containment member.

The absorbent article 10, 110, 210, 310 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. As an example, FIGS. 3A and 3B depict the bodyside liner 28 bonded to the outer cover 26 with adhesive 27. The outer cover 26 can define a length in a longitudinal direction 30, and a width in the lateral direction 32, which, in the illustrated embodiment, can coincide with the length and width of the absorbent article 10, 110, 210. As illustrated in FIGS. 2, 10, 12, and 15, the absorbent article 10, 110, 210, 310 can have a longitudinal axis 29 extending in the longitudinal direction 30 and a lateral axis 31 extending in the lateral direction 32.

Figure 4:
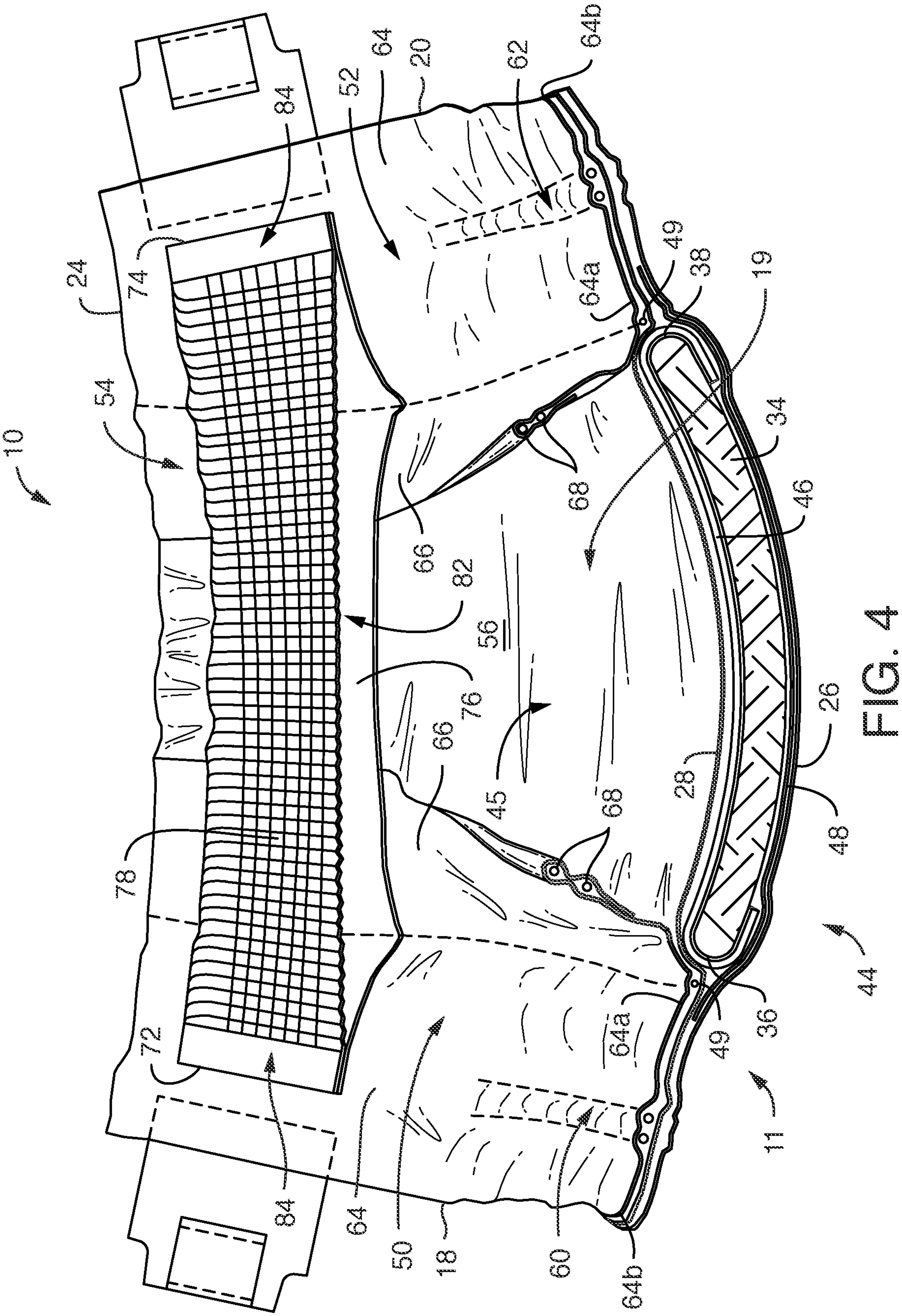
FIG. 4 is a front perspective cross-sectional view taken along line 4-4 from FIG. 2, with the absorbent article being in a relaxed configuration.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 110, 210, 310. The absorbent body 34 can have a first end edge 40 that is opposite a second end edge 42, respectively, which, in an embodiment, can form portions of the waist edges, 22 and 24, respectively, of the absorbent article 10, 110, 210. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 110, 210, 310. The bodyside liner 28, the outer cover 26, and the absorbent body 34 can form part of an absorbent assembly 44. In the absorbent article 310 of FIGS. 14 and 15, the absorbent panel 17 can form the absorbent assembly 44. The absorbent assembly 44 can also include a fluid transfer layer 46 (as shown in FIG. 4) and a fluid acquisition layer (not shown) between the bodyside liner 28 and the fluid transfer layer 46 as is known in the art. The absorbent assembly 44 can also include a spacer layer 48 (as shown in FIG. 4) disposed between the absorbent body 34 and the outer cover 26.

The absorbent article 10, 110, 210, 310 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 110, 210, 310 can suitably include a waist containment member 54. In some embodiments, the waist containment member 54 can be disposed in the rear waist region 14 of the absorbent article 10, 110, 210, 310. Although not depicted herein, it is contemplated that the waist containment member 54 can be additionally or alternatively disposed in the front waist region 12 of the absorbent article 10, 110, 210, 310.

The waist containment member 54 can be disposed on the body facing surface 19 of the chassis 11 to help contain and/or absorb body exudates. In some embodiments, such as in the absorbent articles 10, 110, 210 depicted in FIGS. 2, 4, 10, and 12, the waist containment member 54 can be disposed on the body facing surface 45 of the absorbent assembly 44. In some embodiments, the waist containment member 54 can be disposed on the body facing surface 56 of the bodyside liner 28. In some embodiments, such as in the absorbent article 310 depicted in FIGS. 14 and 15, the waist containment member 54 can be disposed on the body facing surface 58 of the rear waist panel 15.

The absorbent article 10, 110, 210, 310 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 110, 210, 310. The leg elastic members 60, 62 can be parallel to the longitudinal axis 29 as shown in FIGS. 2, 10, 12, and 15 or can be curved as is known in the art. The leg elastic members 60, 62 can provide elasticized leg cuffs.

Additional details regarding each of these elements of the absorbent article 10, 110, 210, 310 described herein can be found below and with reference to the FIGS. 1-15.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110, 210, 310. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110, 210, 310 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 110, 210, 310. The absorbent body 34 can have a length and width that can be less than or equal to the length and width of the absorbent article 10, 110, 210, 310.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 4. The absorbent body 34 can be bonded to the fluid transfer layer 46 and/or the spacer layer 48.

Bodyside Liner:

The bodyside liner 28 of the absorbent article 10, 110, 210, 310 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length, for example, as depicted in the embodiments illustrated in FIGS. 1-13. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 110, 210, 310. In other aspects, the bodyside liner 28 can be stretchable, and more suitably elastic, in both the lateral and the longitudinal directions 32, 30, respectively.

Containment Flaps:

In an embodiment, the absorbent article 10, 110, 210, 310 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110, 210, 310 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, 110, through the crotch region 16 to the rear waist region 14 of the absorbent article 10. In some embodiments, the containment flaps 50, 52 can extend in a direction substantially parallel to the longitudinal axis 29 of the absorbent article 10, 110, 210, however, in other embodiments, the containment flaps 50, 52 can be curved, as is known in the art. In other embodiments, such as the absorbent article 310 in FIGS. 14 and 15, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28 with a barrier adhesive 49, as shown in FIG. 4. 4 or the containment flaps 50, 52 can be bonded to the outer cover 26 with a barrier adhesive 49 in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64*a* and a distal end 64*b*. The projection portion 66 can be separated from the base portion 64 at the proximal end 64*a* of the base portion 64. As used in this context, the projection portion 66 is separated from the base portion 64 at the proximal end 64*a* of the base portion 64 in that the proximal end 64*a* of the base portion 64 defines a transition between the projection portion 66 and the base portion 64. The proximal end 64*a* of the base portion 64 can be located near the barrier adhesive 49. In some embodiments, the distal ends 64*b* of the base portion 64 can laterally extend to the respective longitudinal side edges 18, 20 of the absorbent article 10, 110, 210. In other embodiments, the distal ends 64*b* of the base portion 64 can end laterally inward of the respective longitudinal side edges 18, 20 of the absorbent article 10, 110, 210, 310. The containment flaps 50, 52 can also each include a projection portion 66 that is configured to extend away from the body facing surface 19 of the chassis 11 at least in the crotch region 16 when the absorbent article 10, 110, 210 is in a relaxed configuration, as illustrated in FIG. 4. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIGS. 2, 10, and 12 depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10, 110, 210. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 71 in either or both of the front and rear waist regions 12, 14, respectively. Of course, other configurations of containment flaps 50, 52 can be used in the absorbent article 10, 110, 210, 310 and still remain within the scope of this disclosure.

The containment flaps 50, 52 can include one or more flap elastic members 68, such as the two flap elastic strands depicted in FIGS. 2, 4, 10, and 12. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIGS. 2, 4, 10, and 12, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, 110, 210, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIGS. 2, 10 and 12 for containment flap 50, which will gather upon relaxation of the absorbent article 10, 110. The active flap elastic region 70 of containment flaps 50, 52 can be of a longitudinal length that is less than the length of the absorbent article 10, 110, 210, 310. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10, 110, 210. As noted above, the relaxing of the elastic members 68 in the active flap elastic region 70 when the absorbent article 10, 110, 210, 310 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIG. 4.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110, 210, 310. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIG. 4, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110, 210, 310 without departing from the scope of this disclosure.

Figure 11A:
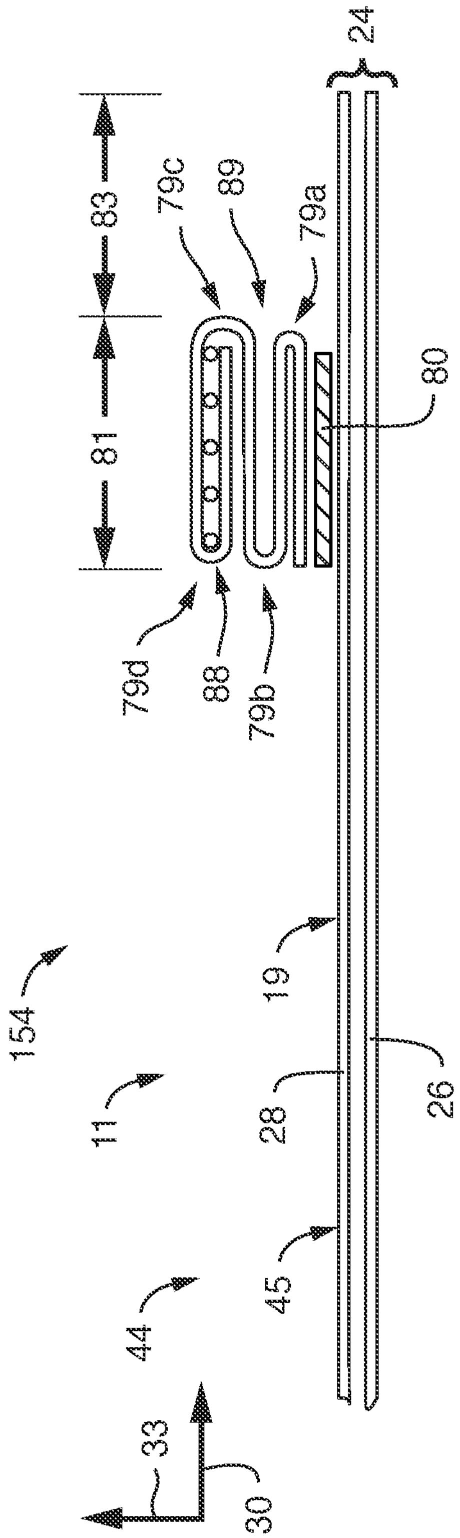
FIG. 11A is a cross-sectional view taken along line 11-11 from FIG. 10.
Figure 11B:
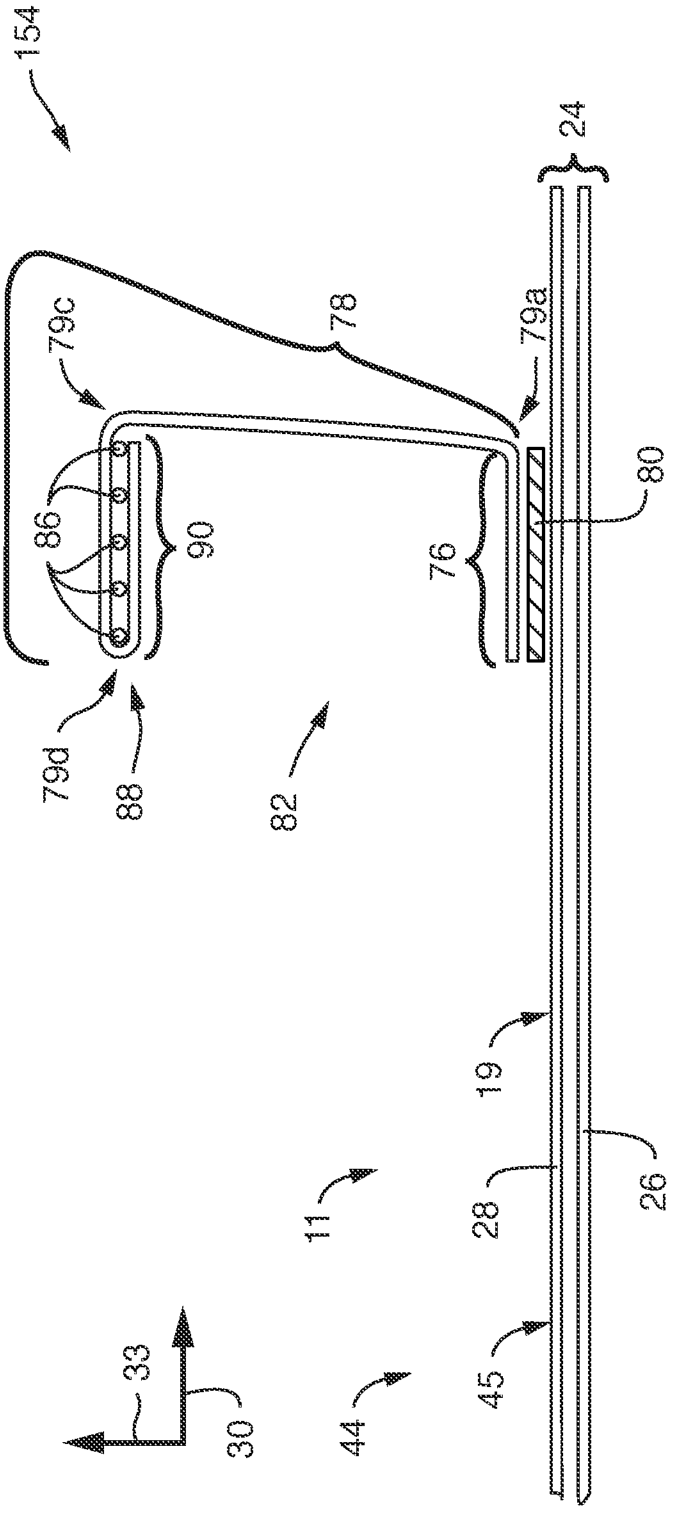
FIG. 11B is a cross-sectional view similar to FIG. 11A, but with the waist containment member being shown in a relaxed configuration.
Figure 13A:
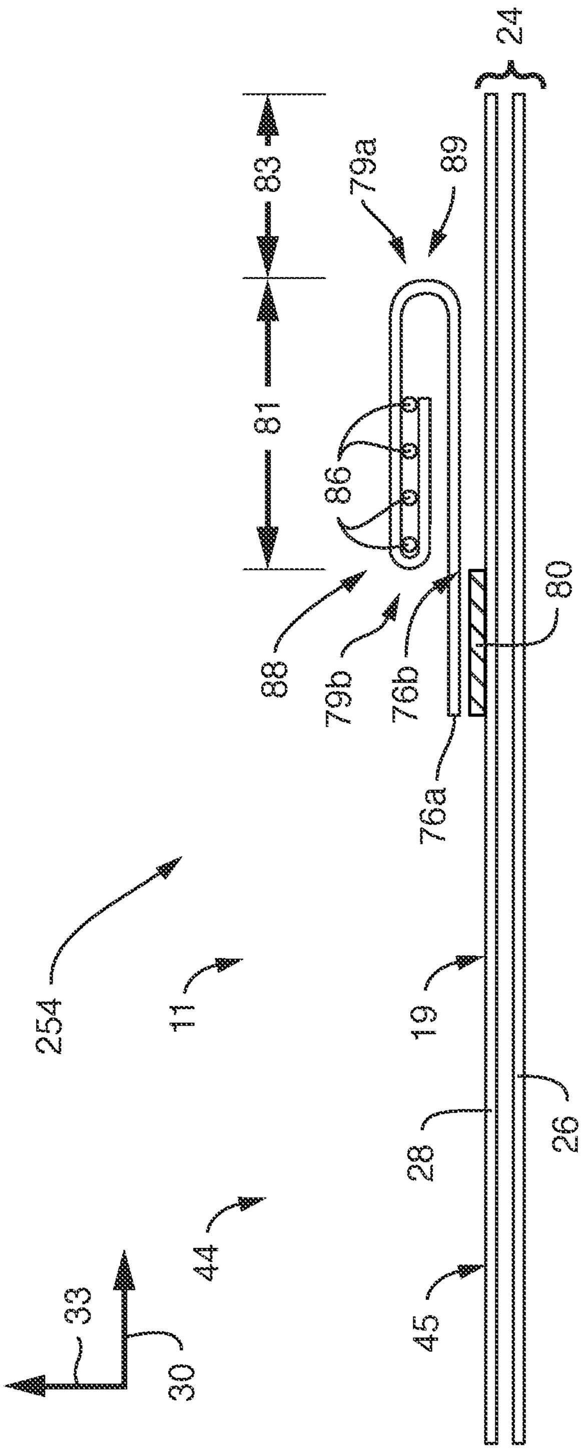
FIG. 13A is a cross-sectional view taken along line 13-13 from FIG. 12.
Figure 13B:
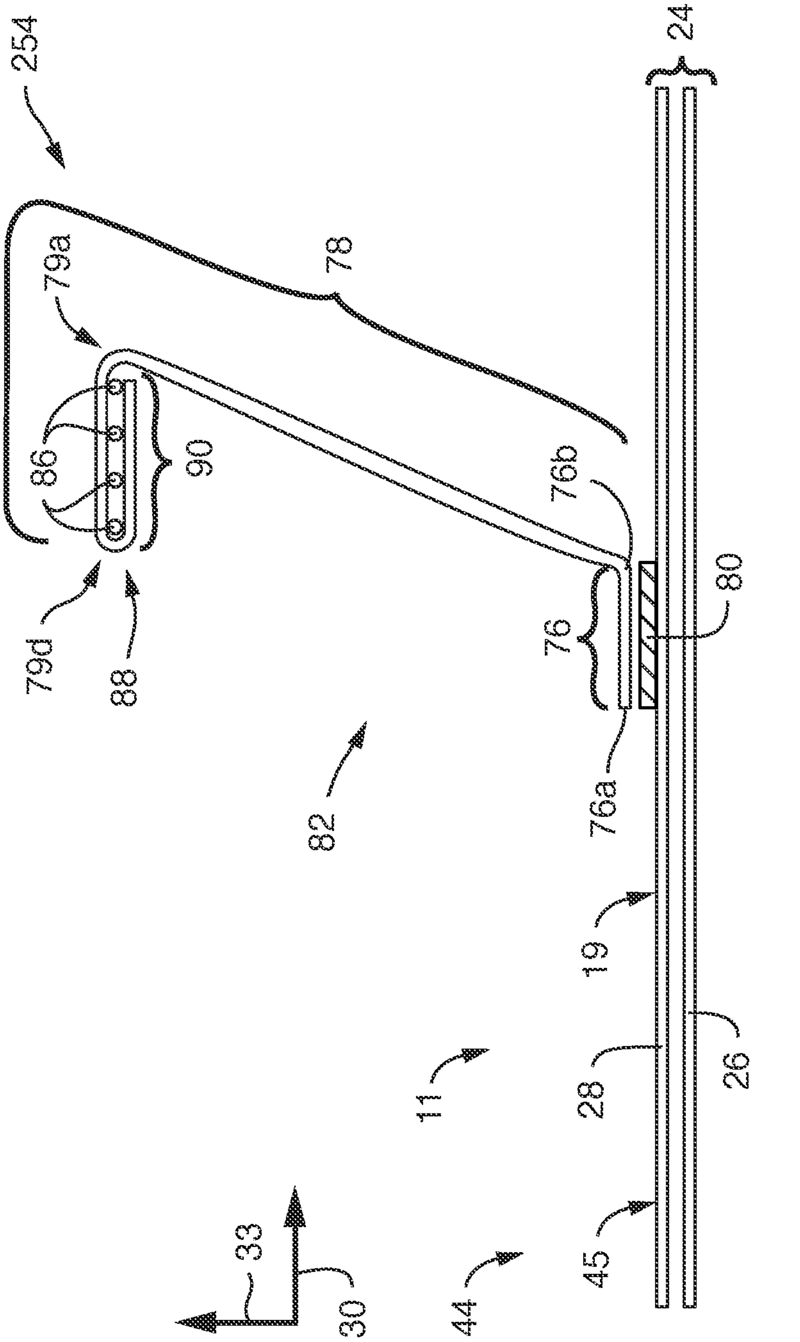
FIG. 13B is a cross-sectional view similar to FIG. 13A, but with the waist containment member being shown in a relaxed configuration.

Waist Containment Member:

In an embodiment, the absorbent article 10, 110, 210, 310 can have one or more waist containment members 54, 154, 254. FIGS. 1-4, 14, and 15 depict an absorbent article 10, 310 with a first embodiment of a waist containment member 54. FIGS. 10-11B depict an absorbent article 110 with another embodiment of a waist containment member 154. FIGS. 12-13B depict an absorbent article 210 with still another embodiment of a waist containment member 254.

The waist containment member(s) 54, 154, 254 can be disposed in the rear waist region 14 as illustrated in FIGS. 1-4 and 10-15. As will be discussed in more detail below, the waist containment member 54, 154, 254 can help contain and/or absorb body exudates, especially low viscosity fecal matter, and as such, can be preferred to be in the rear waist region 14. In some embodiments, the absorbent article 10, 110, 210, 310 can have a waist containment member 54, 154, 254 disposed in the front waist region 12. A waist containment member 54, 154, 254 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54, 154, 254 disposed in the front waist region 12 can help contain and/or absorb body exudates as well. In other embodiments, the absorbent article 10, 110, 210, 310 can have a waist containment member 54, 154, 254 in both the rear waist region 14 and the front waist region 12.

In some embodiments, the waist containment member 54, 154, 254 can be disposed on the body facing surface 45 of the absorbent assembly 44. In some embodiments, such as in embodiments illustrated in FIGS. 1-4 and 10-13B, the waist containment member 54, 154, 254 can be disposed on the body facing surface 56 of the bodyside liner 28. However, in some embodiments, such as the absorbent article 310 in FIG. 15, the waist containment member 54 can be disposed on a body facing surface 58 of the rear waist panel 15.

The waist containment member 54, 154, 254 can include a first longitudinal side edge 72 and a second longitudinal side edge 74. The first longitudinal side edge 72 can be opposite from the second longitudinal side edge 74. The distance between the first longitudinal side edge 72 and the second longitudinal side edge 74 can define a width 51 of the waist containment member 54, 154, 254 in the lateral direction 32, as shown in FIG. 2. Although not depicted, in some embodiments, the first longitudinal side edge 72 can substantially align with the first longitudinal side edge 18 of the absorbent article 10, 110, 210. Similarly, in some embodiments, the second longitudinal side edge 74 can align with the second longitudinal side edge 20 of the absorbent article 10, 110, 210. As illustrated in FIGS. 2, 10, 12, and 15, the waist containment member 54, 154, 254 can be configured such that the first longitudinal side edge 72 can be disposed laterally outward of the proximal end 64*a* of the base portion 64 of the containment flap 50. Similarly, the waist containment member 54, 154, 254 can be configured such that the second longitudinal side edge 74 can be disposed laterally outward of the proximal end 64*a* of the base portion 64 of the containment flap 52.

In various embodiments, the waist containment member 54, 154, 254 can also include a proximal portion 76 and a distal portion 78. The proximal portion 76 can be coupled to the body facing surface 19 of chassis 11 (e.g., the body facing surface 45 of the absorbent assembly 44 or the body facing surface 56 of the bodyside liner 28) whereas the distal portion 78 of the waist containment member 54, 154, 254 can be free to move with respect to the chassis 11 and the absorbent assembly 44 when the absorbent article 10, 110, 210, 310 is in the relaxed configuration, such as shown in FIG. 4. FIG. 3A provides a cross-sectional view of the waist containment member 54 of FIG. 2 and FIG. 3B provides an alternative embodiment of a waist containment member 54, however, in both FIGS. 3A and 3B, the waist containment member 54 is depicted in a relaxed configuration, such that the distal portion 78 can be seen extending away from the chassis 11 and absorbent assembly 44 in a vertical direction 33, which is perpendicular to the plane defined by the longitudinal axis 29 and the lateral axis 31. A fold 79*a* can separate the proximal portion 76 from the distal portion 78 in the various embodiments of the waist containment member 54, 154, 254 discussed herein. As used in this context, the fold 79*a* separates the proximal portion 76 from the distal portion 78 in that the fold 79*a* defines a transition between the proximal portion 76 and the distal portion 78.

The proximal portion 76 can be coupled to the body facing surface 19 of the chassis 11 with an adhesive 80, and in some embodiments, the proximal portion 76 can be coupled to the body facing surface 45 of the absorbent assembly 44. In some embodiments, such as in embodiments illustrated in FIGS. 2-4 and 10-13B, the proximal portion 76 of the waist containment member 54, 154, 254 can be coupled to the body facing surface 56 of the bodyside liner 28. However, in some embodiments, such as the absorbent article 310 in FIG. 15, the proximal portion 76 of the waist containment member 54 can be coupled to the body facing surface 58 of the rear waist panel 15. As illustrated in the examples shown in FIGS. 3A and 3B, the proximal portion 76 can be coupled to the body facing surface 45 of the absorbent assembly 44 with adhesive 80 along the entire length of the proximal portion 76 in the longitudinal direction 30, however, it can be contemplated that only a portion of the proximal portion 76 in the longitudinal direction 30 is coupled to the body facing surface 45 of the absorbent assembly 44. Of course, it is contemplated that the proximal portion 76 of the waist containment member 54, 154, 254 can be coupled to the body facing surface 19 of the chassis 11 or the body facing surface 45 of the absorbent assembly 44 by means other than an adhesive 80, such as by pressure bonding, ultrasonic bonding, thermal bonding, and combinations thereof. In preferred embodiments, the proximal portion 76 is coupled to the body facing surface 19 of the chassis 11 in the lateral direction 32 in a constant fashion, as opposed to an intermittent fashion, such that a barrier to body exudates is formed between the proximal portion 76 and the body facing surface 19 of the chassis 11.

As illustrated in the embodiment depicted in FIG. 3B, the proximal portion 76 of the waist containment member 54 can include a longitudinal length measured in the longitudinal direction 30 that is shorter than a longitudinal length of the distal portion 78 of the waist containment member 54. However in some embodiments, the longitudinal length of the proximal portion 76 can be substantially equal to or larger than the longitudinal length of the distal portion 78 of the waist containment member 54, 154, 254. For purposes herein, the longitudinal length of the proximal portion 76 and the longitudinal length of the distal portion 78 of the waist containment member 54, 154, 254 are measured when the absorbent article 10, 110, 210, 310 is in the stretched, laid flat configuration. It can be appreciated that the relative longitudinal lengths of the proximal portion 76 and the distal portion 78 can be varied between embodiments of the waist containment member 54, 154, 254 without departing from the scope of this disclosure.

As illustrated in FIG. 3A, 3B, because the distal portion 78 of the waist containment member 54 can freely move with respect to the absorbent assembly 44 when the absorbent article 10, is in the relaxed configuration, the distal portion 78 can help provide a containment pocket 82 when the absorbent article 10 is in the relaxed configuration. The containment pocket 82 can help provide a barrier to contain and/or can help absorb body exudates. This containment pocket 82 is also shown with respect to waist containment members 154, 254 in absorbent articles 110, 210 when the waist containment members 154, 254, respectively, are in a relaxed configuration in FIGS. 11B and 13B, which will be discussed further below. The containment pocket 82 can be especially beneficial for containing and/or absorbing low viscosity fecal matter, which can be prevalent in younger children. The first longitudinal side edge 72 can be disposed laterally outward of the proximal end 64*a* of the base portion 64 of the containment flap 50, and thus, the pocket 82 can extend laterally outward of the proximal end 64*a* of the containment flap 50. Similarly, the second longitudinal side edge 74 can be disposed laterally outward of the proximal end 64*a* of the base portion 64 of the containment flap 52 and the pocket 82 can extend laterally outward of the proximal end 64*a* of the containment flap 52. Such a configuration provides waist containment member 54, 154, 254 with a wide containment pocket 82 to contain and/or absorb body exudates. To help prevent lateral flow of body exudates that are contained by the containment pocket 82 of the waist containment member 54, the distal portion 78 of the waist containment member 54 can be bonded to the proximal portion 76 of the waist containment member 54, 154, 254 and/or the body facing surface 19 of the chassis 11 near the first and second longitudinal side edges 72, 74, respectively. For example, FIGS. 2, 4, 10, 12, and 15 depict tack-down regions 84 where the distal portion 78 of the waist containment member 54 can be bonded to the proximal portion 76 of the waist containment member 54 and/or the body facing surface 19 of the chassis 11 near the first and second longitudinal side edges 72, 74, respectively.

In some embodiments, the width 51 of the waist containment member 54, 154, 254 in the lateral direction 32 as compared to the width 53 of the chassis 11 (as labeled in FIG. 2) can have a ratio of about 0.85 to about 1.00. In some embodiments, the width 51 of the waist containment member 54, 154, 254 in the lateral direction 32 as compared to the width 53 of the chassis 11 can have a ratio of about 0.87 to about 1.00. And in other embodiments, the waist containment member 54, 154, 254 in the lateral direction 32 as compared to the width 53 of the chassis 11 can have a ratio of about 0.90 to about 1.00. For purposes herein, the width 53 of the chassis 11 for use in this ratio is the width 53 of the chassis 11 in the waist region in which the waist containment member 54, 154, 254 is disposed and both width measurements are taken in a direction parallel to the lateral direction 32. Thus, for the examples illustrated herein, the width 51 of the waist containment member 54, 154, 254 can be compared to the width 53 of the chassis 11 in the rear waist region 14. Additionally, the width 51 of the waist containment member 54 in the lateral direction 32 and the width 53 of the chassis 11 as discussed for the ratios herein are to be measured when the absorbent article 10, 110, 210, 310 is in the stretched, laid flat configuration.

In preferred embodiments, the waist containment member 54, 154, 254 can include at least one elastic member 86. In some embodiments, such as the embodiments depicted in FIGS. 3A and 3B, the waist containment member 54 can include multiple elastic members 86, such as five elastic members 86. Similarly, the waist containment member 154 as depicted in FIGS. 10-11B also includes five elastic members 86. The waist containment member 254 as depicted in FIGS. 12-13B includes four elastic members 86. Of course, it is contemplated that the waist containment member 54, 154, 254 can include other amounts of elastic members 86, and in some embodiments, no elastic members 86. In some embodiments, the elastic members 86 can be spaced evenly in the longitudinal direction 30 in the distal portion 78 of the waist containment member 54, 154, 254. The elastic member 86 can span substantially from the first longitudinal side edge 72 to the second longitudinal side edge 74 of the waist containment member 54, 154, 254. The elastic member 86 can be disposed in the distal portion 78 of the waist containment member 54, 154, 254, and preferably, is located near a free edge 88 of the distal portion 78 of the waist containment member 54, 154, 254. As illustrated in FIGS. 3A, 3B, 11A, 11B, 13A, and 13B, in some preferred embodiments, the elastic member(s) 86 can be disposed within a laminate portion 90 of the distal portion 78 of the waist containment member 54, 154, 254 to aid in containing the elastic member(s) 86. The laminate portion 90 can be disposed near the free edge 88 of the distal portion 78 of the waist containment member 54, 154, 254. In some embodiments, the laminate portion 90 can be formed by a fold near the free edge 88 of the distal portion 78. For example, in FIGS. 3A and 3B, the laminate portion 90 can be formed by a fold 79*b* in the distal portion 78 at the free edge 88 of the waist containment member 54. In FIGS. 11A and 11B, the laminate portion 90 can be formed by a fold 79*d* in the distal portion 78 of the waist containment member 154, and in FIGS. 13A and 13B, the laminate portion 90 can be formed by a fold 79*b* in the waist containment member 254. The tack-down regions 84, if present, can help retain the elastic member(s) 86, if present, in place, as well as help retain free edge 88 in place.

A wide variety of elastic materials may be used for the elastic member(s) 86 in the waist containment member 54, 154, 254. Suitable elastic materials can include sheets, strands or ribbons of natural rubber, synthetic rubber, thermoplastic elastomeric materials, or elastic foams. The elastic materials can be stretched and secured to a substrate forming the waist containment member 54, 154, 254, secured to a gathered substrate, or secured to a substrate and then elasticized or shrunk, for example, with the application of heat, such that the elastic retractive forces are imparted to the substrate forming the waist containment member 54, 154, 254.

As depicted in FIGS. 2, 10, 12, and 15, in some embodiments the waist containment member 54, 154, 254 can be disposed on the body facing surface 19 of the chassis 11 such that a gap 85 is provided between the second end edge 42 of the absorbent body 34 and the free edge 88 of the distal portion 78 of the waist containment member 54, 154, 254. By providing a gap 85, the containment pocket 82 can have a greater void volume for body exudates. Additionally, it is believed that gap 85 can help body exudates enter the containment pocket 82 of the waist containment member 54.

The waist containment member 54 can be disposed to be coupled to the chassis 11 by being placed either over the containment flaps 50, 52 or under the containment flaps 50, 52. More specifically, as shown in FIGS. 2, 4, 10, 12, and 15, the waist containment member 54, 154, 254 can be disposed on the body facing surface 19 of the chassis 11 such that the proximal portion 76 of the waist containment member 54, 154, 254 is disposed over the base portion 64 of the first and the second containment flaps 50, 52, respectively. Alternatively, the waist containment member 54, 154, 254 can be disposed on the body facing surface 19 of the chassis 11 such that the proximal portion 76 of the waist containment member 54, 154, 254 is disposed under the base portion 64 of the first and the second containment flaps 50, 52, respectively. Both configurations can provide advantages to the functioning of the waist containment member 54 to contain and/or absorb body exudates.

Embodiments where the proximal portion 76 of the waist containment member 54, 154, 254 is disposed over the base portion 64 of the containment flaps 50, 52 can provide the advantage that the containment flaps 50, 52 can help the distal portion 78 of the waist containment member 54, 154, 254 extend away from the body facing surface 45 of the absorbent assembly 44 when the absorbent article 10, 110, 210, 310 is applied to the wearer. This is especially relevant where the proximal portion 76 of the waist containment member 54, 154, 254 has a shorter longitudinal length than the distal portion 78 of the waist containment member 54. For example, in FIG. 3B, because the proximal portion 76 is shorter than the distal portion 78, the flap elastics 68 in the projection portion 66 of the containment flaps 50, 52 can provide an opening force on the distal portion 78 of the waist containment member 54 when the absorbent article 10 is in the relaxed configuration and applied to the wearer, thus helping the distal portion 78 extend away from the body facing surface 45 of the absorbent assembly 44 and opening the containment pocket 82. In some embodiments, the containment pocket 82 can be additionally or alternatively opened by configuring the containment flaps 50, 52 to have an active flap elastic region 70 that longitudinally overlaps with the distal portion 78 of the waist containment member 54 when the absorbent article 10 is in the stretched, laid flat configuration, such as illustrated in FIG. 2. Additionally or alternatively, the containment pocket 82 of the waist containment member 54 can be opened by configuring the containment flaps 50, 52 to have a tack-down region 71 that does not extend to the free edge 88 of the distal portion 78 of the waist containment member 54, such as illustrated in FIGS. 2, 10, and 12. However, such a configuration of the tack-down region 71 is not required, and in some embodiments, the tack-down region 71 can extend from the rear waist edge 24 past the free edge 88 of the distal portion 78 of the waist containment member 54.

Embodiments where the proximal portion 76 of the waist containment member 54, 154, 254 is disposed under the base portion 64 of the containment flaps 50, 52 can provide the advantage of having the containment pocket 82 formed by the waist containment member 54, 154, 254 be free from the projection portion 66 of the containment flaps 50, 52. Both the base portion 64 and the projection portion 66 of each containment flap 50, 52 can be coupled to the body facing surface 55 of the waist containment member 54, 154, 254. As a result, body exudates may more freely spread through the full width of the containment pocket 82 created by the waist containment member 54, 154, 254. Additionally, the coupling of the base portion 64 of the containment flaps 50, 52 to the outer cover 26 (or in some embodiments to the bodyside liner 28) can create a longitudinal barrier to the flow of body exudates out of the containment pocket 82 for exudates that spread laterally beyond the location of the barrier adhesive 49. In some embodiments, the tack-down region 71 of the projection portion 66 of each of the containment flaps 50, 52 can longitudinally overlap with the distal portion 78 of the waist containment member 54, 154, 254. In some embodiments, the tack-down region 71 of projection portion 66 of each of the containment flaps 50, 52 can extend to the free edge 88 of the waist containment member 54, 154, 254 to further assist in containing exudates within the containment pocket 82 created by the waist containment member 54, 154, 254.

The free edge 88 of the distal portion 78 of the waist containment member 54, 154, 254 can be selectively positioned on the body facing surface 19 of the chassis 11 with respect to the rear waist edge 24 of the absorbent article 10, 110, 210, 310 to provide enhanced containment properties for body exudates. By providing the free edge 88 of the distal portion 78 of the waist containment member 54, 154, 254 at a selective location with respect to the rear waist edge 24, the free edge 88 of the waist containment member 54, 154, 254 can be positioned to provide the best skin contact with the wearer across the width 51 of the waist containment member 54, 154, 254 to prevent exudates from leaking from the absorbent article 10, 110, 210, 310 in the wearer's small of the back region 67. In some embodiments configured to be worn by young children, the free edge 88 of the distal portion 78 of the waist containment member 54, 154, 254 can be about 50.0 millimeters or less from the rear waist edge 24. In some embodiments, the free edge 88 of the distal portion 78 of the waist containment member 54, 154, 254 can be about 40.0 millimeters or less from the rear waist edge 24. And in other embodiments, the free edge 88 of the distal portion 78 of the waist containment member 54, 154, 254 can be about 30.0 millimeters or less from the rear waist edge 24. For purposes herein, the measurement of the free edge 88 of the distal portion 78 of the waist containment member 54, 154, 254 to the rear waist edge 24 of the absorbent article 10, 110, 210, 310 is to be measured when the absorbent article 10, 110, 210, 310 is in the stretched, laid-flat configuration.

Figure 5:
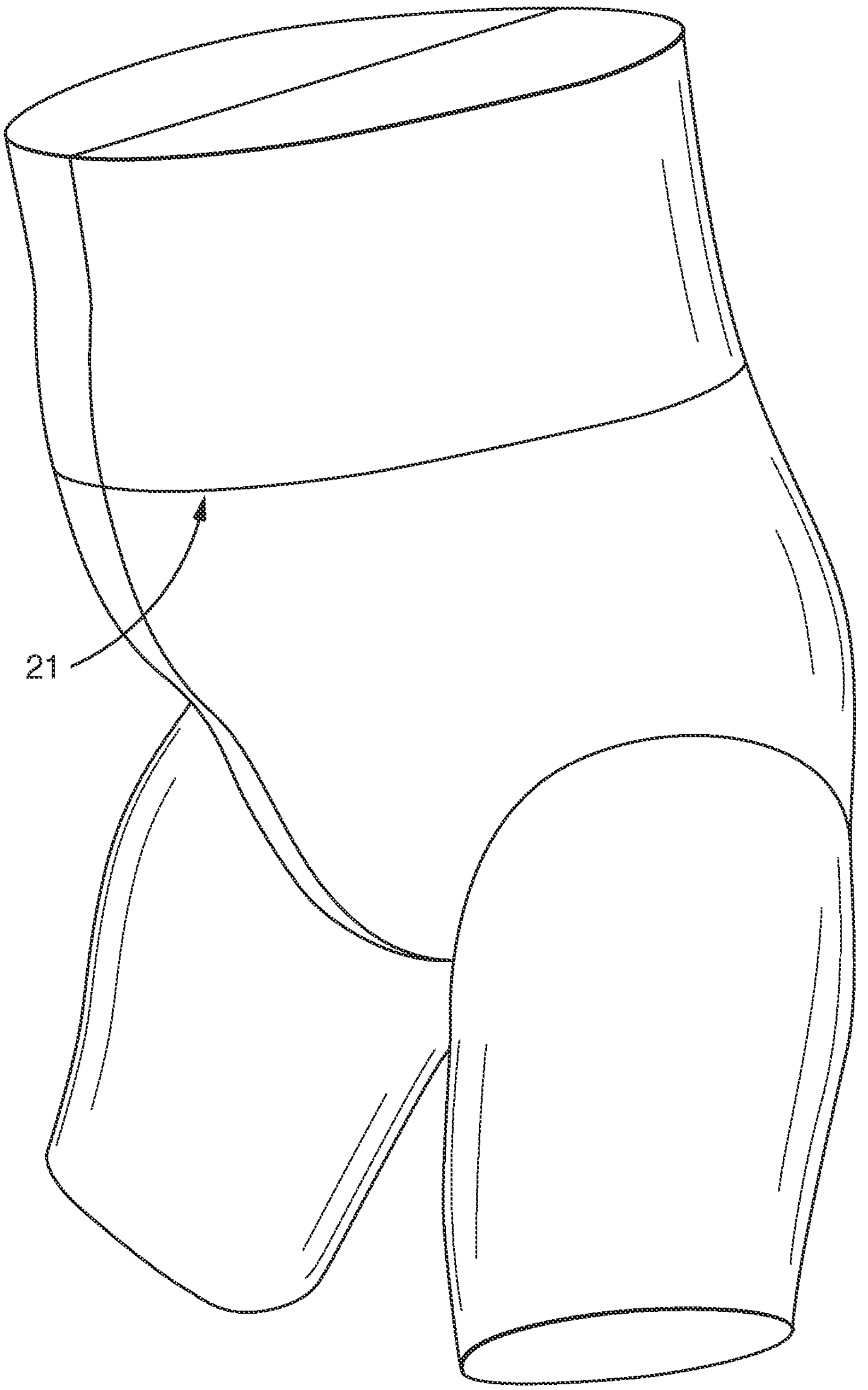
FIG. 5 is a perspective view of a torso of a wearer.
Figure 6:
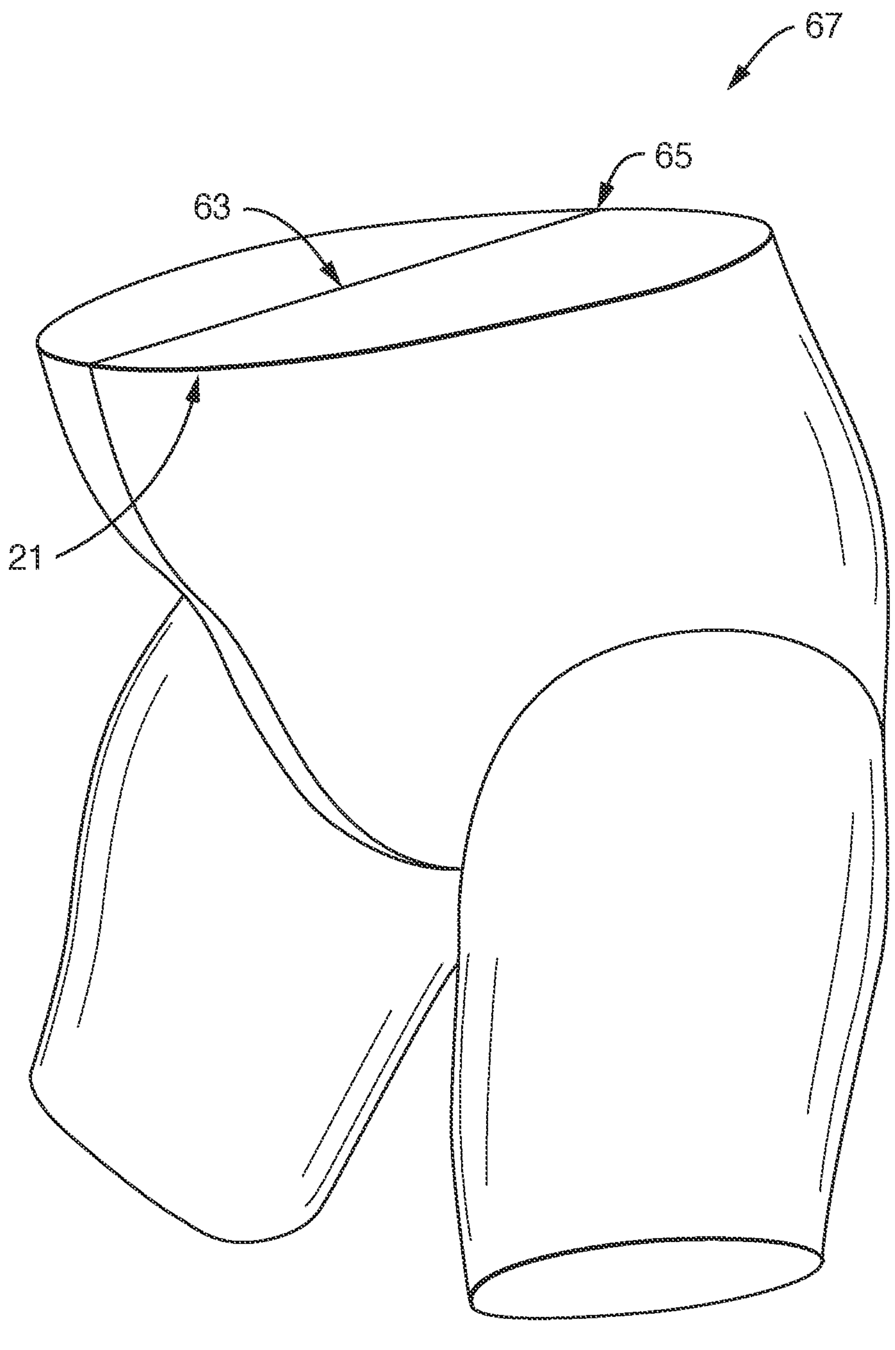
FIG. 6 is a perspective view of a torso of FIG. 5, with a cross-section taken at the waistline.

Turning to FIGS. 5-9, a series of anthropometric studies and data provide further understanding for why the selective location of the free edge 88 of the distal portion 78 of the waist containment member 54, 154, 254 can provide the benefit of reducing body exudates leaking from the absorbent article 10, 110, 210, 310. FIG. 5 depicts a digitized torso of a wearer, representative of an infant that is in the mid-range of a step 2 size diaper, approximately 15. 7 pounds and 10 months old. The approximate waistline position 21 for where the front waist edge 22 and rear waist edge 24 would be located for a properly fitted absorbent article 10, 110, 210, 310 is shown. FIG. 6 provides a perspective view of the digitized torso of FIG. 5, with a cross-section taken at the waistline 21. FIG. 6 shows a bisection line 63 that bisects the torso. Point 65 is located where the bisection line 63 intersects the waistline 21 in the small of the back region 67 of the torso.

Figure 7:
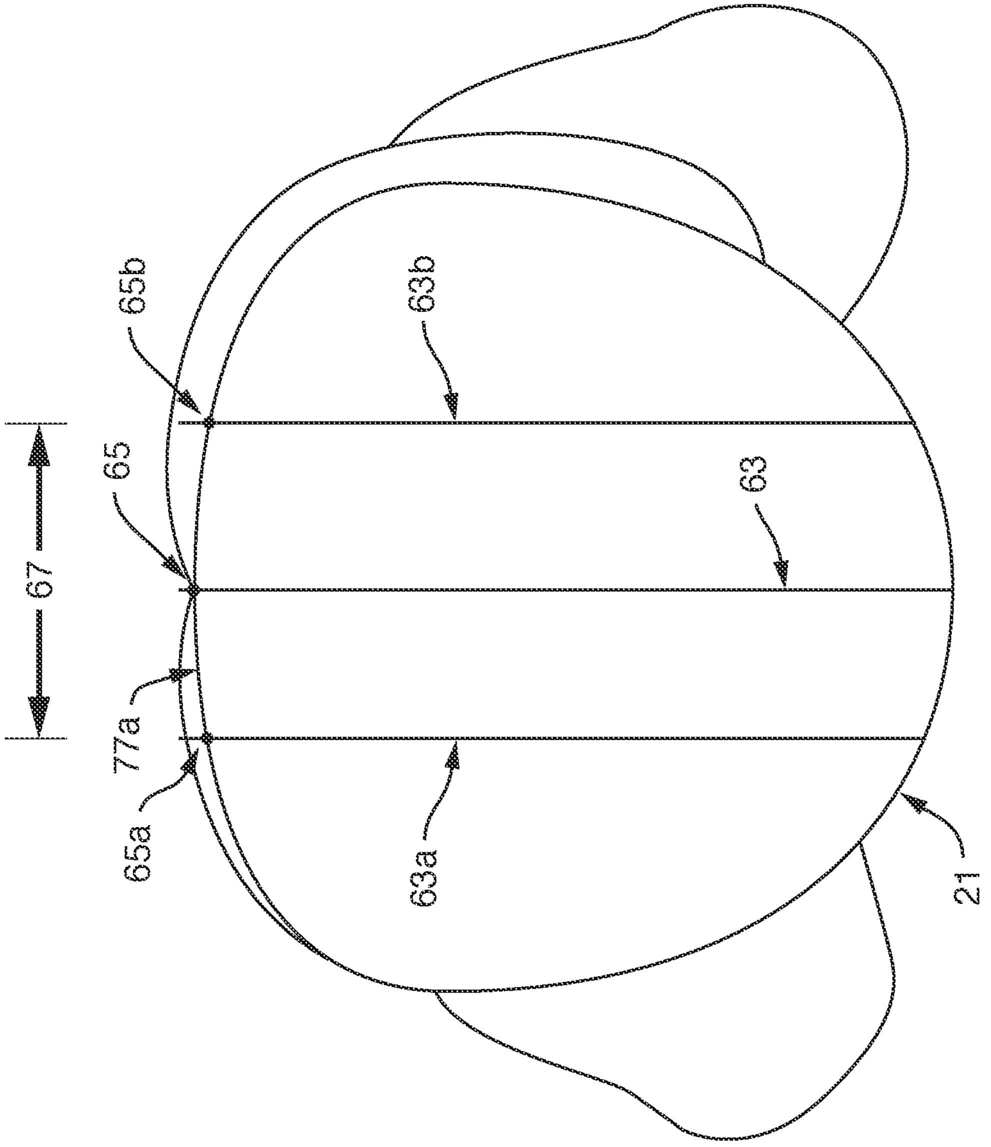
FIG. 7 is a top view of the torso of FIG. 6.

FIG. 7 provides a top plan view of the torso from FIG. 6 and shows point 65 at the intersection of the bisection line 63 with the waistline 21 in the small of the back region 67 of the wearer. As illustrated in FIG. 7, the small of the back region 67 at this location on the wearer's torso has a convex configuration. Two lines 63*a* and 63*b* are shown as being parallel to bisection line 63. Lines 63*a* and 63*b* are each spaced 25.0 mm, respectively, on opposite sides of the bisection line 63 and define the width of the small of the back region 67. The lines 63*a* and 63*b* intersect the waistline 21 of the torso at points 65*a* and 65*b*, respectively. A profile 77*a* of the back region of the torso of FIG. 5 is thus defined between points 65*a* and 65*b*, passing through point 65.

Figure 8A:
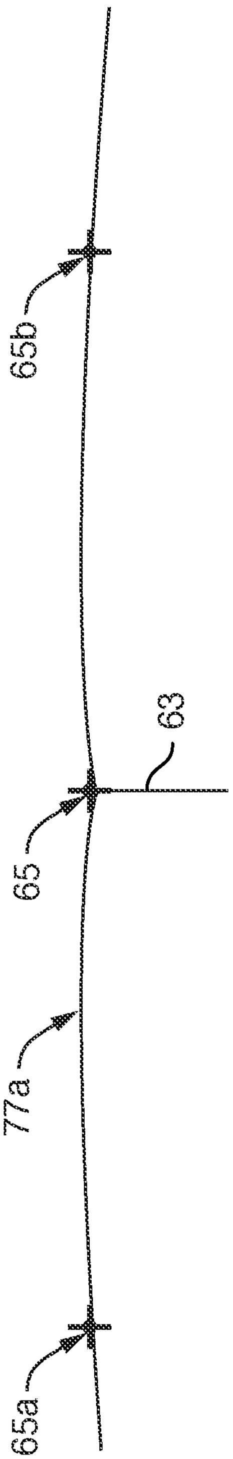
FIG. 8A is a profile of the back region of the torso of FIG. 5 viewed from a top plan view, with the profile being taken at the waistline as shown in FIG. 7.
Figure 8B:
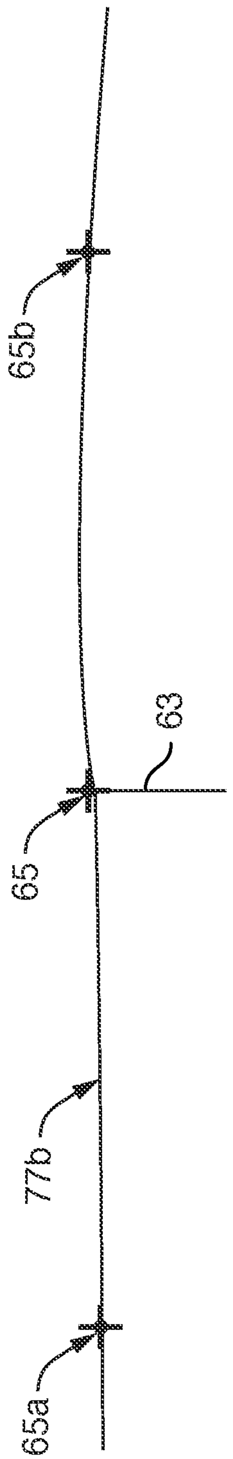
FIG. 8B is a profile of the back region of the torso of FIG. 5 viewed from a top plan view, with the profile being taken 25 millimeters below the waistline.
Figure 8C:
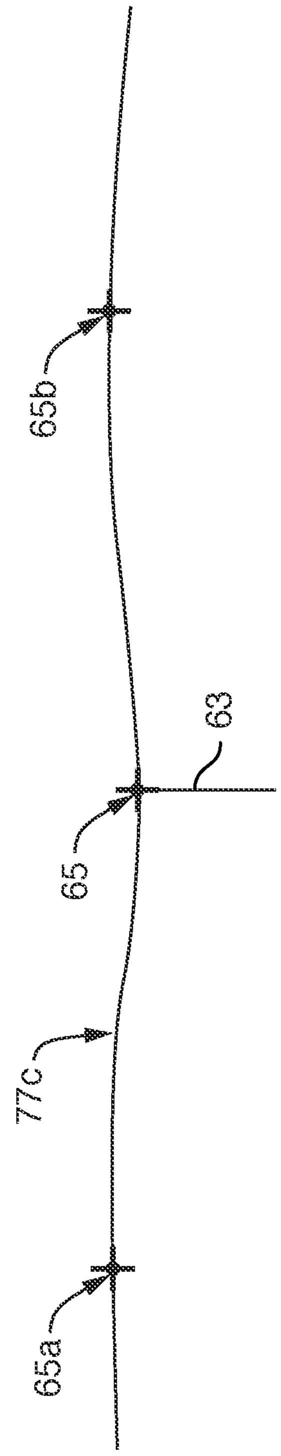
FIG. 8C is a profile of the back region of the torso of FIG. 5 viewed from a top plan view, with the profile being taken 50 millimeters below the waistline.
Figure 8D:
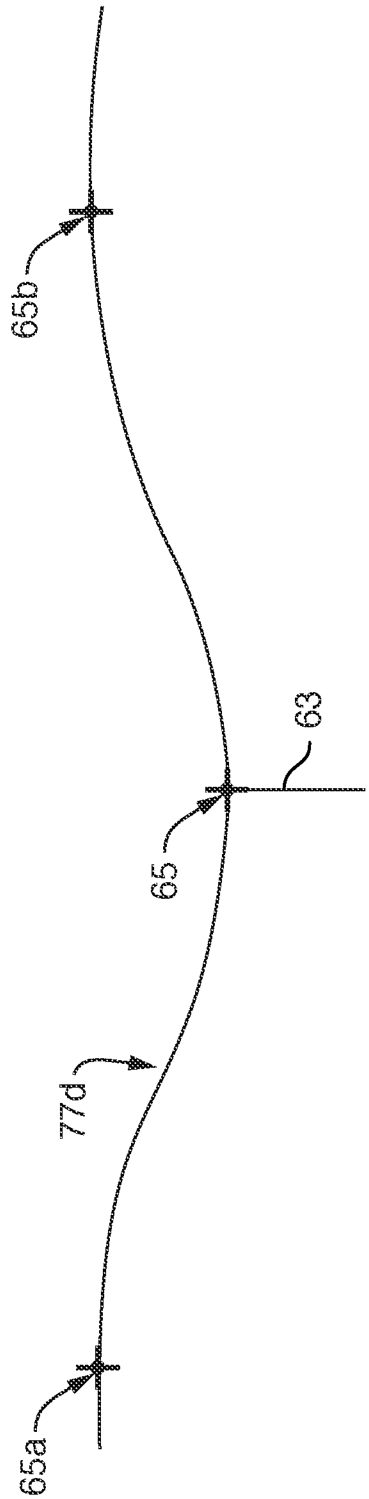
FIG. 8D is a profile of the back region of the torso of FIG. 5 viewed from a top plan view, with the profile being taken 75 millimeters below the waistline.

FIGS. 8A-8D provides profiles 77*a*, 77*b*, 77*c*, 77*d* of the back region of the torso from FIG. 5 at various cross-sections of the torso relative to the waistline 21, extending between points 65*a* and 65*b* discussed above. FIG. 8A provides the profile 77*a* of the back region of the torso of FIG. 5 at the cross-section taken right at the waistline 21. FIG. 8B provides a profile 77*b* of the back region of the torso taken 25.0 mm below the waistline 21. FIG. 8C provides a profile 77*c* of the back region of the torso taken 50.0 mm below the waistline 21. FIG. 8D provides a profile 77*d* of the back region of the torso taken 75.0 mm below the waistline 21. FIGS. 8A-8D depict how the torso transitions from a generally linear or slightly convex shape to a concave shape.

Viewing FIGS. 8A and 8B, it can be seen that the torso in the back region has a generally linear, or slightly convex profile 77*a*, 77*b* when viewed at the waistline 21 (FIG. 8A) and 25.0 mm below the waistline 21 (FIG. 8B). However, a concave nature in the profiles 77*c* and 77*d* in the back region of the torso can be seen when the torso is viewed at 50.0 mm below the waistline 21 (FIG. 8C) and 75.0 mm below the waistline 21 (FIG. 8D). The concave nature of the torso along profiles 77*c* and 77*d* depicts the gluteal depression on the torso. The gluteal depression provides a passage for body exudates to escape from an absorbent article, possibly soiling the wearer's back, clothing, sheets, or that of a caregiver. The depth of the gluteal depression at point 65 can be measured using modeling techniques for this torso, as well as other torsos.

Table 1 below shows the values of the depth of the gluteal depression for three representative wearer torsos as the distance from the waistline 21 increases. For example, the "Step 2 Girl" is the wearer's torso as illustrated in FIGS. 5-7 and shown in profiles 8A-8D and discussed above. The "Step 4 Girl" is of a 5th percentile for the step 4 size diaper, approximately 23.5 pounds. The "Step 4 Boy" is of a 75th percentile for the step 4 size diaper, approximately 34.4 pounds. Referring to Table 1 below, a negative value for the gluteal depression means that the profile including point 65 where the bisection line 63 intersects the small of the back region 67 is convex, such as discussed above and illustrated in FIG. 8A. Positive values for gluteal depression means that the profile including point 65 where the bisection line 63 intersects the small of the back region 67 is concave, such as discussed above and illustrated in FIGS. 8C and 8D.

TABLE 1

| Distance from | Depth of Gluteal Depression (mm) | | |
|---|---|---|---|
| diaper line (mm) | Step 2 Girl | Step 4 Girl | Step 4 Boy |
| 0 | −0.16 | −0.87 | −3.31 |
| 5 | −0.62 | −1.56 | −3.38 |
| 10 | −0.52 | −1.43 | −3.31 |
| 15 | −0.08 | −2.28 | −2.59 |
| 20 | −0.25 | −1.75 | −2.08 |
| 25 | −0.26 | −1.65 | −0.48 |
| 30 | 0.10 | −1.60 | 1.14 |
| 35 | 0.20 | −1.21 | 2.79 |
| 40 | 0.02 | −0.71 | 5.18 |
| 45 | 0.33 | 0.76 | 7.17 |
| 50 | 0.54 | 2.68 | 8.35 |
| 55 | 1.17 | 5.89 | 9.60 |
| 60 | 2.49 | 6.95 | 10.17 |
| 65 | 3.04 | 8.35 | 10.33 |
| 70 | 3.41 | 9.05 | 10.24 |

TABLE 1-continued

| Distance from | Depth of Gluteal Depression (mm) | | |
|---|---|---|---|
| diaper line (mm) | Step 2 Girl | Step 4 Girl | Step 4 Boy |
| 75 | 3.37 | 9.34 | 9.55 |
| 80 | 3.66 | 10.06 | 9.55 |

Figure 9:
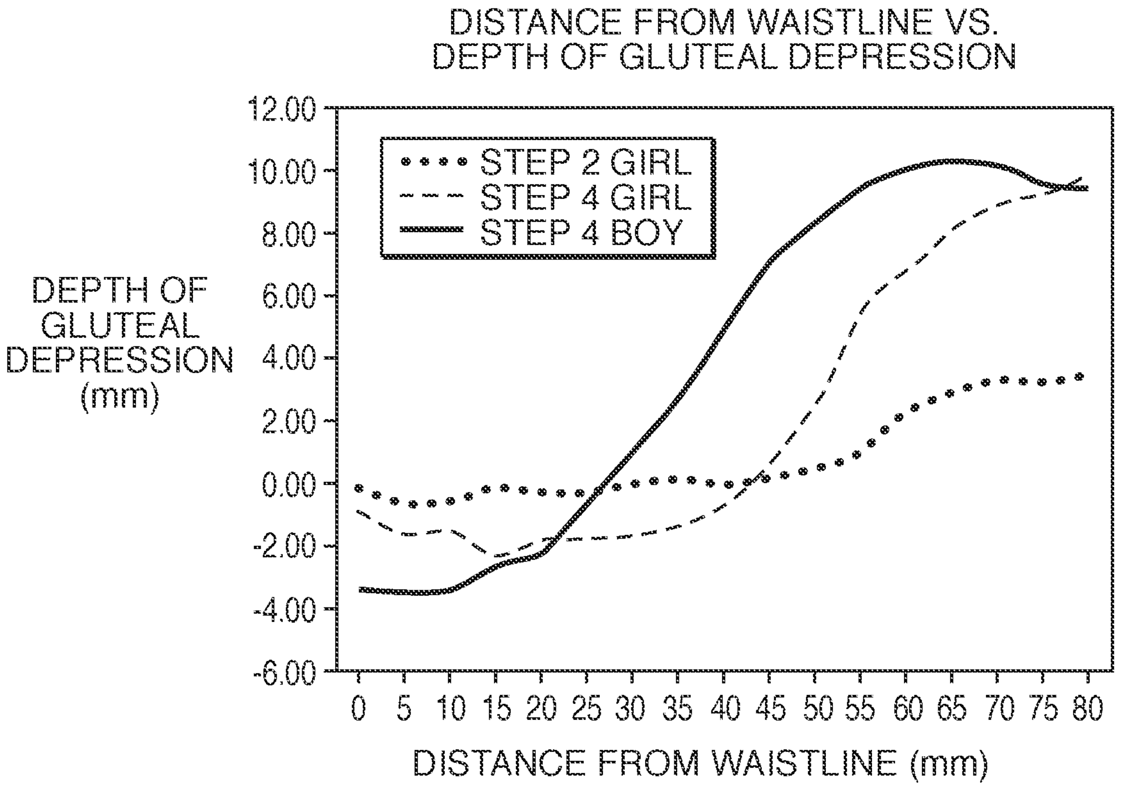
FIG. 9 is a graph depicting the distance from waistline vs. depth of gluteal depression values from Table 1

FIG. 9 provides a graphical illustration for the depth of the gluteal depression values from Table 1. As illustrated in FIG. 9, it is apparent that for at least the representative samples analyzed for Step 2 Girl, Step 4 Girl, and Step 4 Boy, the depth of the gluteal depression increases at a greater rate once the distance from the diaper line reaches about 30.0 mm to about 50.0 mm below the waistline 21. Based on this anthropometric analysis, in some embodiments it can be preferable to have the waist containment member 54, 154, 254 disposed in the rear waist region 14 such that the free edge 88 of the distal portion 78 is less than about 50.0 mm from the rear waist edge 24 of the absorbent article 10, 110, 210, especially for absorbent articles 10, 110, 210 that are configured as diapers and intended to be worn by young children. More preferably, the free edge 88 of the distal portion 78 is less than about 40.0 mm from the rear waist edge 24 of the absorbent article 10, 110, 210, and even more preferably, the free edge 88 of the distal portion 78 is less than about 30.0 mm from the rear waist edge 24 of the absorbent article 10, 110, 210. Configuring the waist containment member 54, 154, 254 in such a fashion can provide better contact of the free edge 88 of the distal portion 78 of the waist containment member 54, 154, 254 against the wearer's skin along the entire width 51 of the waist containment member 54, 154, 254, and thus, reduce the possibility of body exudates escaping from the absorbent article 10, 110, 210, 310. Of course, it is contemplated that the free edge 88 of the distal portion 78 can be more than about 50.0 mm from the rear waist edge 24 of the absorbent article 10, 110, 210 and still be within the scope of this disclosure. It can also be appreciated that a wearer's profile in the back region can vary from individual to individual, as well as from different age classes of individuals.

Configuring the free edge 88 of the waist containment member 54, 154, 254 can in some circumstances, reduce the void volume or volume of the containment pocket 82 for containing and/or absorbing the body exudates. However, referring to FIGS. 10-13B, two embodiments of alternative waist containment members 154, 254 will now be described that are configured to still maintain adequate void volume in a containment pocket 82 yet still retain the free edge 88 within close proximity to the rear waist edge 24 as discussed above.

Turning first to the waist containment member 154 on absorbent article 110 in FIGS. 10-11B, the waist containment member 154 can be configured to be disposed in the rear waist region 14. The waist containment member 154 can include at least three folds when the absorbent article 110 is in the stretched, laid flat configuration, such as illustrated in FIGS. 10 and 11A. The waist containment member 154 of FIG. 11A provides for four folds 79*a*, 79*b*, 79*c*, and 79*d*. Each of the folds 79*a*, 79*b*, 79*c*, and 79*d* can fold the waist containment member 154 in a direction generally parallel to the lateral axis 31 of the absorbent article 110. As discussed above with respect to other embodiments, fold 79*a* can separate the distal portion 78 of the waist containment member 154 from the proximal portion 76 of the waist containment member 154. However, for purposes herein, fold 79*a* can be considered to be within the distal portion 78 of the waist containment member 154. Thus, in some embodiments, the distal portion 78 can includes four folds 79*a*, 79*b*, 79*c*, 79*d*. As shown in FIGS. 10 and 11A, the folded nature of the waist containment member 154 can keep the free edge 88 close to the rear waist edge 24 to provide the benefits of a better fit to the wearer's skin, and thus preventing exudates from leaking from the absorbent article 110, by staying above the gluteal depression. For example, in an exemplary embodiment, the folded longitudinal length 81 of the waist containment member 154 as measured in the longitudinal direction 30 from the free edge 88 to the top edge 89 of the waist containment member 154 can be about 15.0 mm. The folded waist containment member 154 can have an offset distance 83 of about 10.0 mm from the rear waist edge 24, as measured between the top edge 89 and the rear waist edge 24. Thus, the free edge 88 can be about 25.0 mm from the rear waist edge 24.

FIG. 11B illustrates the waist containment member 154 when the absorbent article 110 is in a relaxed configuration, in which the distal portion 78 can extend away from the body facing surface 19 of the chassis 11 (e.g., the body facing surface 45 of the absorbent assembly 44). By including at least three folds 79*a*, 79*b*, 79*c* in the waist containment member 154, the waist containment member 154 can extend in the vertical direction 33 to create void volume for body exudates to be contained and/or absorbed by the waist containment member 154, yet still remain compact with respect to the rear waist edge 24, as described above. The additional folds 79*b*, 79*c* in the waist containment member 154, as compared to the waist containment member 54 discussed above and shown in FIGS. 3A and 3B, provide for this additional vertical height of the waist containment member 154 while still remaining close to the rear waist edge 24.

FIGS. 12-13B depict another embodiment of a waist containment member 254 that can provide adequate void volume for the containment pocket 82 of the waist containment member 254, yet still provide the free edge 88 of the distal portion 78 of the waist containment member 254 within the desired distance of the rear waist edge 24. This can be accomplished by the waist containment member 254 by asymmetric folding, or the selective location of fold 79*a*. As illustrated in FIGS. 13A and 13B, the proximal portion 76 can include a first edge 76*a* and a second edge 76*b*. The second edge 76*b* of the proximal portion 76 can define a transition between the proximal portion 76 and the distal portion 78 of the waist containment member 254. The second edge 76*b* can be located at the end of the adhesive 80 that couples the proximal portion 76 to the body facing surface 19 of the chassis 11 (e.g., body facing surface 45 of the absorbent assembly 44).

As depicted in FIG. 13A, the free edge 88 of the distal portion 78 can be closer to the rear waist edge 24 than is the first edge 76*a* of the proximal portion 76 of the waist containment member 254 when the absorbent article 210 is in the stretched, laid flat configuration. In some embodiments, the free edge 88 of the distal portion can be about the same distance from the rear waist edge 24 as the second edge 76*b* of the proximal portion 76 of the waist containment member 254 is when the absorbent article 210 is in the stretched, laid flat configuration, such as illustrated in FIG. 13A. In other words, in some embodiments, the free edge 88 can substantially align with the second edge 76*b* of the proximal portion 76 of the waist containment member 254 when the absorbent article 210 is in the stretched, laid flat configuration. Although not depicted, it is also contemplated that in some embodiments, the free edge 88 can be closer to the rear waist edge 24 than is the second edge 76*b* of the proximal portion 76 of the waist containment member 254. In the embodiment depicted in FIG. 13A, the folded longitudinal length 81 of the waist containment member 254 as measured from the free edge 88 to the top edge 89 of the waist containment member 254 can be about 20.0 mm. The folded waist containment member 254 can have an offset distance 83 of about 10.0 mm from the rear waist edge 24, as measured between the top edge 89 and the rear waist edge 24. Thus, the free edge 88 of the waist containment member 254 can be about 30.0 mm from the rear waist edge 24.

As depicted in FIG. 13B, by asymmetrically folding the waist containment member 254 such that the free edge 88 of the distal portion 78 is closer to the rear waist edge 24 than is the first edge 76*a* of the proximal portion 76, the free edge 88 can extend away from the body facing surface 19 of the chassis 11 (e.g., the body facing surface 45 of the absorbent assembly 44) when the absorbent article 210 is in a relaxed configuration and the waist containment member 254 can provide adequate void volume for the containment pocket 82, yet still keep the free edge 88 in close proximity to the rear waist edge 24 of the absorbent article 210 to provide a close fit to the wearer's skin across the width 51 of the waist containment member 254 above the gluteal depression. The tack-down regions 84, as discussed above, can be helpful in retaining the positioning of the free edge 88 with respect to the rear waist edge 24 as the free edge 88 of the waist containment member 254 lifts when the absorbent article 210 is in the relaxed configuration as shown in FIG. 13B.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. The basis weight of the material forming the waist containment member 54 can vary, however, in a preferred embodiment, the basis weight can be between about 8 gsm to about 120 gsm, not including the elastic members 86 in the waist containment member 54. More preferably, the basis weight of the material comprising the waist containment member 54 can be between about 10 gsm to about 40 gsm, and even more preferably, between about 15 gsm to about 25 gsm.

Fastening System:

In an embodiment, the absorbent article 10, 110, 210 can include a fastening system. The fastening system can include one or more back fasteners 91 and one or more front fasteners 92. The embodiments being shown in FIGS. 1, 2, 10, and 12 depict embodiments with one front fastener 92. Portions of the fastening system may be included in the front waist region 12, rear waist region 14, or both.

The fastening system can be configured to secure the absorbent article 10, 110, 210 about the waist of the wearer in a fastened condition as shown in FIG. 1 and help maintain the absorbent article 10, 110, 210 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIGS. 2, 10, and 12. In some embodiments the waist containment member 54, 154, 254 can laterally extend to the back fasteners 91, and/or to each of the longitudinal side edges 18, 20 of the absorbent article 10, 110, 210, 310. In some embodiments, the waist containment member 54, 154, 254 can be coupled to the stretch component 94 of the back fasteners 91, either directly or indirectly.

EMBODIMENTS

Embodiment 1: An absorbent article including a front waist region including a front waist edge, a rear waist region including a rear waist edge, a crotch region, a longitudinal axis and a lateral axis, the absorbent article comprising: a chassis including an absorbent body, the chassis including a body facing surface; and a waist containment member disposed on the body facing surface of the chassis, the waist containment member comprising: a first longitudinal side edge and a second longitudinal side edge; a proximal portion coupled to the body facing surface of the chassis; a distal portion including a free edge, the distal portion being free to move with respect to the chassis when the absorbent article is in a relaxed configuration; and at least three folds when the absorbent article is in a stretched, laid-flat configuration, each of the at least three folds folding the waist containment member in a direction generally parallel to the lateral axis of the absorbent article.

Embodiment 2: An absorbent article including a front waist region including a front waist edge, a rear waist region including a rear waist edge, a crotch region, a longitudinal axis and a lateral axis, the absorbent article comprising: a chassis including an absorbent body, the chassis including a body facing surface; and a waist containment member disposed on the body facing surface of the chassis, the waist containment member comprising: a first longitudinal side edge and a second longitudinal side edge; a proximal portion including a first edge and a second edge, the proximal portion being coupled to the body facing surface of the absorbent assembly; and a distal portion including a free edge, the distal portion being free to move with respect to the chassis when the absorbent article is in a relaxed configuration, the second edge of the proximal portion of the waist containment member defining a transition between the proximal portion and the distal portion, the free edge of the distal portion being closer to the rear waist edge than is the first edge of the proximal portion of the waist containment member when the absorbent article is in a stretched, laid-flat configuration.

Embodiment 3: An absorbent article including a front waist region including a front waist edge, a rear waist region including a rear waist edge, a crotch region, a longitudinal axis and a lateral axis, the absorbent article comprising: a chassis including an absorbent body, the chassis including a body facing surface; and a waist containment member disposed on the body facing surface of the chassis, the waist containment member comprising: a first longitudinal side edge and a second longitudinal side edge; a proximal portion, the proximal portion being coupled to the body facing surface of the chassis; and a distal portion including a free edge, the distal portion being free to move with respect to the chassis when the absorbent article is in a relaxed configuration, the free edge being about 50.0 millimeters or less from the rear waist edge of the absorbent article when the absorbent article is in the stretched, laid-flat configuration.

Embodiment 4: The absorbent article of any one of embodiments 1-3, wherein the waist containment member includes at least four folds when the absorbent article is in a stretched, laid-flat configuration, each of the at least four folds folding the waist containment member in a direction generally parallel to the lateral axis of the absorbent article.

Embodiment 5: The absorbent article of embodiment 4, wherein the distal portion of the waist containment member includes the at least four folds.

Embodiment 6: The absorbent article of any one of the preceding embodiments, wherein the waist containment member further comprises at least one elastic member.

Embodiment 7: The absorbent article of embodiment 6, wherein the distal portion of the waist containment member includes the at least one elastic member.

Embodiment 8: The absorbent article of embodiment 1 or embodiment 2, wherein the free edge of the distal portion of the waist containment member is about 50.0 millimeters or less from the rear waist edge of the absorbent article when the absorbent article is in the stretched, laid-flat configuration.

Embodiment 9: The absorbent article of embodiment 8, wherein the free edge of the distal portion of the waist containment member is about 40.0 millimeters or less from the rear waist edge of the absorbent article when the absorbent article is in the stretched, laid-flat configuration.

Embodiment 10: The absorbent article of embodiment 3, wherein the free edge of the distal portion of the waist containment member is about 30.0 millimeters or less from the rear waist edge of the absorbent article when the absorbent article is in the stretched, laid-flat configuration.

Embodiment 11: The absorbent article of embodiment 1 or embodiment 3, wherein the proximal portion includes a first edge and a second edge, the second edge defining a transition between the proximal portion and the distal portion of the waist containment member, and wherein the free edge of the distal portion is closer to the rear waist edge than is the first edge of the proximal portion when the absorbent article is in a stretched, laid-flat configuration.

Embodiment 12: The absorbent article of embodiment 2, wherein the free edge of the distal portion is substantially the same distance from the rear waist edge as is the second edge of the proximal portion of the waist containment member when the absorbent article is in a stretched, laid-flat configuration.

Embodiment 13: The absorbent article of embodiment 11, wherein the free edge of the distal portion is substantially the same distance from the rear waist edge as is the second edge of the proximal portion of the waist containment member when the absorbent article is in a stretched, laid-flat configuration.

Embodiment 14: The absorbent article of any one of embodiments 1-5 or 8-13, wherein the distal portion includes a laminate section, the laminate section being near the free edge of the distal portion.

Embodiment 15: The absorbent article of embodiment 14, wherein the waist containment member further comprises at least one elastic member, the at least one elastic member being disposed in the laminate section of the distal portion of the waist containment member.

Embodiment 16: The absorbent article of claim 14, wherein the waist containment member comprises at least three elastic members, the at least three elastic members being disposed in the laminate section of the distal portion of the waist containment member.

Embodiment 17: The absorbent article of any one of the preceding embodiments, wherein the chassis further comprises a bodyside liner and an outer cover, the absorbent body being disposed between the bodyside liner and the outer cover.

Embodiment 18: The absorbent article of embodiment 17, wherein the bodyside liner includes a body facing surface, and wherein the proximal portion of the waist containment member is coupled to the body facing surface of the bodyside liner.

Embodiment 19: The absorbent article of any one of the preceding embodiments, further comprising: a pair of containment flaps including a first containment flap and a second containment flap, the first containment flap being on a first side of the longitudinal axis and the second containment flap being on a second side of the longitudinal axis, the first and second containment flap each comprising: a base portion including a proximal end and a distal end; and a projection portion configured to extend away from the body facing surface of the chassis in at least the crotch region when the absorbent article is in a relaxed condition, the projection portion being separated from the base potion at the proximal end of the base portion.

Embodiment 20: The absorbent article of embodiment 19, wherein the proximal portion of the waist containment member is disposed over the base portion of the first and second containment flaps.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region including a front waist edge, a rear waist region including a rear waist edge, a crotch region, a longitudinal axis and a lateral axis, the absorbent article comprising:

a chassis including an absorbent body, the chassis including a body facing surface; and a waist containment member disposed on the body facing surface of the chassis, the waist containment member comprising:

a first longitudinal side edge and a second longitudinal side edge;

a proximal portion coupled to the body facing surface of the chassis;

a distal portion including a free edge, the distal portion being free to move with respect to the chassis when the absorbent article is in a relaxed configuration; and at least three folds when the absorbent article is in a stretched, laid-flat configuration, each of the at least three folds folding the waist containment member in a direction generally parallel to the lateral axis of the absorbent article.

2. An absorbent article including a front waist region including a front waist edge, a rear waist region including a rear waist edge, a crotch region, a longitudinal axis and a lateral axis, the absorbent article comprising:

a chassis including an absorbent body, the chassis including a body facing surface; and a waist containment member disposed on the body facing surface of the chassis, the waist containment member comprising:

a first longitudinal side edge and a second longitudinal side edge;

a proximal portion including a first end edge and a second end edge, the proximal portion being coupled to the body facing surface of the absorbent assembly between the first end edge and the second end edge; and a distal portion including a free edge, the distal portion being free to move with respect to the chassis when the absorbent article is in a relaxed configuration, the second end edge of the proximal portion of the waist containment member defining a transition between the proximal portion and the distal portion, the free edge of the distal portion being closer to the rear waist edge than is the first end edge of the proximal portion of the waist containment member when the absorbent article is in a stretched, laid-flat configuration, wherein a length of the distal portion extending in the longitudinal direction is greater than a length of the proximal portion extending in the longitudinal direction.

3. An absorbent article including a front waist region including a front waist edge, a rear waist region including a rear waist edge, a crotch region, a longitudinal axis and a lateral axis, the absorbent article comprising:

a chassis including an absorbent body, the chassis including a body facing surface; and a waist containment member disposed on the body facing surface of the chassis and spaced from the rear waist edge, the waist containment member comprising:

a first longitudinal side edge and a second longitudinal side edge;

a proximal portion, the proximal portion being coupled to the body facing surface of the chassis;

a distal portion including a free edge, the distal portion being free to move with respect to the chassis when the absorbent article is in a relaxed configuration, the free edge being about 40.0 millimeters or less from the rear waist edge of the absorbent article when the absorbent article is in a stretched, laid-flat configuration; and a fold defining a transition between the proximal portion and the distal portion, wherein a length of the distal portion extending in the longitudinal direction is greater than a length of the proximal portion extending in the longitudinal direction.

4. The absorbent article of claim 1, wherein the waist containment member includes at least four folds when the absorbent article is in a stretched, laid-flat configuration, each of the at least four folds folding the waist containment member in a direction generally parallel to the lateral axis of the absorbent article.

5. The absorbent article of claim 4, wherein the distal portion of the waist containment member includes the at least four folds.

6. The absorbent article of claim 1, wherein the waist containment member further comprises at least one elastic member.

7. The absorbent article of claim 6, wherein the distal portion of the waist containment member includes the at least one elastic member.

8. The absorbent article of claim 2, wherein the free edge of the distal portion of the waist containment member is about 50.0 millimeters or less from the rear waist edge of the absorbent article when the absorbent article is in the stretched, laid-flat configuration.

9. The absorbent article of claim 8, wherein the free edge of the distal portion of the waist containment member is about 40.0 millimeters or less from the rear waist edge of the absorbent article when the absorbent article is in the stretched, laid-flat configuration.

10. The absorbent article of claim 3, wherein the free edge of the distal portion of the waist containment member is about 30.0 millimeters or less from the rear waist edge of the absorbent article when the absorbent article is in the stretched, laid-flat configuration.

11. The absorbent article of claim 1, wherein the proximal portion includes a first edge and a second edge, the second edge defining a transition between the proximal portion and the distal portion of the waist containment member, and wherein the free edge of the distal portion is closer to the rear waist edge than is the first edge of the proximal portion when the absorbent article is in a stretched, laid-flat configuration.

12. The absorbent article of claim 2, wherein the free edge of the distal portion is substantially the same distance from the rear waist edge as is the second edge of the proximal portion of the waist containment member when the absorbent article is in a stretched, laid-flat configuration.

13. The absorbent article of claim 11, wherein the free edge of the distal portion is substantially the same distance from the rear waist edge as is the second edge of the proximal portion of the waist containment member when the absorbent article is in a stretched, laid-flat configuration.

14. The absorbent article of claim 1, wherein the distal portion includes a laminate section, the laminate section being near the free edge of the distal portion.

15. The absorbent article of claim 14, wherein the waist containment member further comprises at least one elastic member, the at least one elastic member being disposed in the laminate section of the distal portion of the waist containment member.

16. The absorbent article of claim 14, wherein the waist containment member comprises at least three elastic members, the at least three elastic members being disposed in the laminate section of the distal portion of the waist containment member.

17. The absorbent article of claim 1, wherein the chassis further comprises a bodyside liner and an outer cover, the absorbent body being disposed between the bodyside liner and the outer cover.

18. The absorbent article of claim 17, wherein the bodyside liner includes a body facing surface, and wherein the proximal portion of the waist containment member is coupled to the body facing surface of the bodyside liner.

19. The absorbent article of claim 1, further comprising:

a pair of containment flaps including a first containment flap and a second containment flap, the first containment flap being on a first side of the longitudinal axis and the second containment flap being on a second side of the longitudinal axis, the first and second containment flap each comprising:

a base portion including a proximal end and a distal end; and a projection portion configured to extend away from the body facing surface of the chassis in at least the crotch region when the absorbent article is in a relaxed condition, the projection portion being separated from the base potion at the proximal end of the base portion.

20. The absorbent article of claim 19, wherein the proximal portion of the waist containment member is disposed over the base portion of the first and second containment flaps.

* * * * *